United States Patent
Chan et al.

(10) Patent No.: US 10,815,189 B2
(45) Date of Patent: Oct. 27, 2020

(54) METHOD FOR PRODUCING NITROBENZENE

(71) Applicant: Covestro Deutschland AG, Leverkusen (DE)

(72) Inventors: Denise Chan, Düsseldorf (DE); Thomas Knauf, Dormagen (DE); Juergen Muennig, Kaarst (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/491,287

(22) PCT Filed: Mar. 5, 2018

(86) PCT No.: PCT/EP2018/055376
§ 371 (c)(1),
(2) Date: Sep. 5, 2019

(87) PCT Pub. No.: WO2018/162427
PCT Pub. Date: Sep. 13, 2018

(65) Prior Publication Data
US 2020/0017434 A1 Jan. 16, 2020

(30) Foreign Application Priority Data
Mar. 7, 2017 (EP) .................................... 17159723

(51) Int. Cl.
*C07C 201/08* (2006.01)
*C07C 201/16* (2006.01)

(52) U.S. Cl.
CPC .......... *C07C 201/08* (2013.01); *C07C 201/16* (2013.01)

(58) Field of Classification Search
CPC .... C07C 201/06; C07C 201/08; C07C 205/06
See application file for complete search history.

(56) References Cited

U.S. PATENT DOCUMENTS

| 4,091,042 | A | 5/1978 | Alexanderson et al. |
| 4,772,757 | A | 9/1988 | Lailach et al. |
| 5,313,009 | A | 5/1994 | Guenkel et al. |
| 5,616,818 | A | 4/1997 | Pirkl et al. |
| 5,763,697 | A | 6/1998 | Hermann et al. |
| 6,288,289 | B1 | 9/2001 | Boyd et al. |
| 6,562,247 | B2 | 5/2003 | Gillis et al. |
| 2003/0055300 | A1 | 3/2003 | Chrisochoou et al. |
| 2005/0224424 | A1 | 10/2005 | Knauf et al. |
| 2007/0249873 | A1 | 10/2007 | Knauf et al. |
| 2010/0076230 | A1 | 3/2010 | Knauf et al. |
| 2011/0196177 | A1 | 8/2011 | Munnig et al. |
| 2013/0204043 | A1 | 8/2013 | Knauf et al. |
| 2015/0166460 | A1 | 6/2015 | Knauf et al. |
| 2015/0175522 | A1 | 6/2015 | Knauf et al. |
| 2016/0083332 | A1 | 3/2016 | Mairata et al. |
| 2017/0174612 | A1 | 6/2017 | Knauf et al. |

OTHER PUBLICATIONS

Quadros et al., nitrophenols reduction in the benzene adiabatic nitration process (Industrial and Engineering Chemistry Research (2004), 43 (15), 4438-4445).*
International Search Report, PCT/EP2018/055376, dated May 9, 2018, Authorized officer: Thomas Stroeter.

* cited by examiner

*Primary Examiner* — Jafar F Parsa
(74) *Attorney, Agent, or Firm* — Donald R. Palladino

(57) ABSTRACT

The invention relates to a method for continuous production of nitrobenzene by means of nitration of benzene with nitric acid and sulfuric acid, in which load change (i.e. a reduction or increase in the quantity of nitric acid supplied to the process per time interval) is particularly advantageously developed. The invention particularly relates to a method in which, in the case of a load reduction, the ratio of the masses of benzene and nitric acid supplied per time interval is significantly increased compared to said ratio before the load change and/or the ratio of the masses of nitric acid and sulfuric acid supplied per time interval is significantly reduced compared to said ratio before the load change. In the event of a load increase, the reverse is carried out.

15 Claims, No Drawings

METHOD FOR PRODUCING NITROBENZENE

CROSS-REFERENCE TO RELATED APPLICATION

This application is a national stage application under 35 U.S.C. § 371 of PCT/EP2018/055376, filed Mar. 5, 2018, which claims the benefit of European Application No. 17159723, filed Mar. 7, 2017, each of which is incorporated herein by reference.

FIELD

The invention relates to a process for continuously producing nitrobenzene by nitrating benzene with nitric acid and sulfuric acid, in which changes in load (i.e. an increase or decrease in the amount of nitric acid supplied to the process per unit time) are configured particularly advantageously. More particularly, the present invention relates to a process in which, in the event of a decrease in load, the ratio of the masses of benzene and nitric acid supplied per unit time is significantly increased compared to this ratio prior to the change in load and/or the ratio of the masses of nitric acid and sulfuric acid supplied per unit time is significantly decreased compared to this ratio prior to the change in load. The reverse procedure is followed in the case of an increase in load.

BACKGROUND

Nitrobenzene (also called mononitrobenzene, MNB) is an important intermediate in the chemical industry which is required particularly for preparation of aniline (ANL) and hence also for preparation of the di- and polyisocyanates of the diphenylmethane series (MDI) and the polyurethanes based thereon.

The current standard processes for nitrating benzene with nitric acid to give nitrobenzene correspond essentially to the concept of the adiabatically operated nitration of benzene by a mixture of sulfuric acid and nitric acid, which is generally referred to as mixed acid. Such a process is described, for example, in EP 0 436 443 B1, EP 0 771 783 B1 and U.S. Pat. No. 6,562,247 B2. A common factor to the adiabatically operated processes described is that the benzene and nitric acid starting materials are reacted in a large excess of nitric acid, which absorbs the heat of reaction released and the water formed in the reaction. The reaction is generally conducted in such a way that the nitric acid and sulfuric acid are combined to give what is called the nitrating acid (also called mixed acid). Benzene is metered into this nitrating acid. The reaction products are essentially water and nitrobenzene. In the nitration reaction, benzene, based on the molar amount of nitric acid, is used at least in a stoichiometric amount, but preferably in a 2% to 10% excess. The crude nitrobenzene formed in the reaction apparatuses and separated from the acid phase in phase separation apparatuses, according to the prior art, is subjected to a scrubbing and a distillative workup, as described, for example, in EP 1 816 117 A1 (page 2 lines 26 to 42), U.S. Pat. No. 4,091,042 (see above) or U.S. Pat. No. 5,763,697. A characteristic feature of this workup is that unconverted excess benzene, after the scrubbing, is separated from nitrobenzene in a final distillation and reused as "return benzene" in the nitration reaction. For this purpose, it is mixed with freshly supplied benzene ("fresh benzene") to give the "feed benzene". The acid phase consisting essentially of sulfuric acid is concentrated in a flash evaporator and very substantially freed of organics. The sulfuric acid concentrated in this way is returned to the nitration as circulated sulfuric acid.

DE 28 21 571 A1 relates to a continuous adiabatic nitration process in which a reaction stream composed of a mixed acid with about 3% to 7.5% nitric acid, about 58.5% to 66.5% sulfuric acid and about 28% to 37% water and a reaction stream with up to an about 10% stoichiometric excess of benzene are mixed continuously and converted with vigorous stirring at a temperature of about 80 to 120° C. at superatmospheric pressure in such a way that the reaction temperature does not exceed about 145° C., which forms mononitrobenzene with a content of less than about 500 ppm of dinitrobenzene with virtually complete conversion of the nitric acid.

WO 2015/197521 A1 describes a process for continuously preparing nitrobenzene by nitrating benzene with a mixture of nitric acid and sulfuric acid, in which, during a production shutdown, rather than running the whole production plant down, the production plant is run wholly or at least partly in circulation. The application further relates to a plant for preparation of nitrobenzene and to a method of operating a plant for preparation of nitrobenzene.

WO 2014/177450 A1 describes a continuously operated adiabatic process for preparing nitrobenzene by nitrating benzene with nitric acid and sulfuric acid, in which the dilute sulfuric acid obtained on completion of nitration and separation of the crude nitrobenzene from the aqueous phase is concentrated for the purpose of reuse in the nitration and, after concentration thereof, is admixed with an oxidizing agent for at least one minute before it comes into contact with fresh nitric acid again so as to establish a concentration of the oxidizing agent of 10 ppm to 5000 ppm, based on the total mass of the concentrated sulfuric acid to be recycled into the nitration.

The startup of the continuous nitrobenzene process is described in WO 2014/016292 A1, wherein, during the startup operation, either a feed benzene containing less than 1.5% aliphatic organic compounds, based on the total amount of the feed benzene, is utilized or solely fresh benzene (that generally meets these specifications demands) is used.

WO 2014/016290 A1 likewise describes the startup operation of a continuous nitrobenzene process, wherein the circulating sulfuric acid is to contain less than 1.0% organic compounds, especially nitrobenzene, based on the total mass of sulfuric acid in the sulfuric acid circuit. This is achieved in that, the at the end of a production cycle or before a new production cycle, the flash evaporator for concentration of the nitric acid is operated at elevated temperature in order in this way to remove nitrobenzene and traces of benzene, dinitrobenzene and nitrophenol from the circulating sulfuric acid.

Isothermal processes for nitration of benzene with mixed acid are additionally known, as described, for example, in EP 0 156 199 B1.

The quality of a reaction process for preparation of nitroaromatics is thus defined firstly by the content of unwanted secondary components and impurities in the crude product that arise from improper conduct of the reaction. Secondly, the quality of a reaction process is defined in that the overall process can be operated without technical production outage or problems that necessitate intervention into the process, and that losses of feedstocks can be avoided or at least minimized.

Industrial scale production plants are optimized for operation at a defined nameplate production capacity (also referred to as "nameplate load"). Nameplate production capacity is defined by the maximum possible throughput for a given production plant of the reactant that determines the yield of desired product, i.e., in the case of the nitration of benzene—since the benzene is used in excess—by the maximum possible throughput of nitric acid (also referred to as nitric acid load) under the boundary conditions chosen for the production plant (especially excess of benzene and amount of sulfuric acid). If, for example, as a result of a fall in demand, the throughput of nitric acid is reduced—i.e. if working in what is called the part-load range—the throughput of the other reactants is typically also reduced correspondingly (i.e. in the same ratio). As taught by operational experience, however, this course of action is not always free of problems.

What is common to all the above-cited literature references is that they do not describe the operating of a continuously operated nitration plant in part-load operation and the associated difficulties. Nor are abovementioned international applications WO 2014/016292 A1 and WO 2014/016290 A1 concerned with changes in load during ongoing production operation. This is because both applications proceed from a state of a non-operational production plant (i.e. the mass flows of benzene, nitric acid and sulfuric acid in the starting state are zero). The period from commencement of continuous production (startup) through the actual continuous production (if at all possible at nameplate load, if required also at lower load) until the ending of continuous production (shutdown) is also referred to as "production cycle". The two patent applications WO 2014/016292 A1 and WO 2014/016290 A1 are concerned with the first part of such a production cycle, the startup, while the present invention is concerned with the middle part, the actual continuous production. The startup described in WO 2014/016292 A1 and WO 2014/016290 A1 has the aim of bringing the production plant as rapidly as possible, but without any problems, to the state of the desired target load (nameplate load).

Changes in load in ongoing operation, i.e. reductions in load especially proceeding from nameplate load to, for example, "half-load" (=50% of nameplate load) or increases in load, for example proceeding from half-load to "three-quarter load" (=75% of nameplate load) are not covered by patent applications WO 2014/016292 A1 and WO 2014/016290 A1. Such changes in load, however, can bring challenges that go beyond those in standard startup operation. The reason for this is ultimately that production plants are optimized for operation at nameplate load and, therefore, the effect of any significant deviation from operation at nameplate load is that a production plant is running only sub-optimally from an economic and/or technical point of view Thus, in the event of a decrease in the nitric acid load in a nitration plant to a value significantly below the nameplate load, there is also a significant increase in the residence time in the reaction apparatuses, to a value for which the production plant has not been optimized. This can be associated with increased by-product formation, under some circumstances associated with increased formation of deposits in the apparatuses used. An increase in load (for example from 50% to 75% of nameplate load) can also be associated with similar problems.

In the event of changes in load in ongoing production operation, therefore, in the starting state or in the final state, in the extreme case in both states, the production plant has to be operated for a substantial period of time—under some circumstances for days or even weeks if, for instance, there is a temporary drop in demand on the market—under conditions for which it has not been optimized. This problem cannot simply be countered by structural adjustments to the production plant. This is because the apparatus-related features of a production plant, after completion thereof, are fixed and no longer variable—or at least not without complex modifications, which one tries to avoid.

SUMMARY

Further improvements in the known processes for preparing nitrobenzene would therefore be desirable. More particularly, it would be desirable to configure the known processes for preparing nitrobenzene such that they can be operated even in part-load ranges without problems, especially with regard to the formation of unwanted by-products or even deposits. In addition, it would be desirable to be able to avoid the complete shutdown of individual production lines as far as possible in the event of reduced demand for the desired nitroaromatics, in order not to allow possible problems in startup and shutdown and possible damage during shutdown periods to occur in the first place. The possibility of operation of a production plant under part-load conditions with avoidance or at least reduction in the above-mentioned problems would also increase flexibility, for instance in that a production plant having two production lines could also be operated without difficulty with, for example, 60% of total nameplate load and not just with 50% (as would be the case in the event of complete shutdown of one of the two production lines and operation of the other production line at nameplate load).

DETAILED DESCRIPTION

Taking account of this requirement, the present invention provides a continuously operated process for preparing nitrobenzene, comprising the nitration of benzene (1) with nitric acid (2) and sulfuric acid (3), in which
  (i) the nitration is supplied with
    a stream 10 containing benzene (1) and having a proportion by mass of benzene (1) of $w_1$, where $w_1$ is preferably ≥0.950, more preferably ≥0.980, with a mass flow rate of $\dot{m}_{10}$,
    a stream 20 containing nitric acid (2) and having a proportion by mass of nitric acid (2) of $w_2$, where $w_2$ is preferably in the range from 0.600 to 0.750, more preferably in the range from 0.650 to 0.700, with a mass flow rate of than and
    a stream 30 containing sulfuric acid (3) and having a proportion by mass of sulfuric acid of $w_3$, where $w_3$ is preferably in the range from 0.650 to 0.750, more preferably in the range from 0.690 to 0.730, with a mass flow rate of firm;
  (ii) $\dot{m}_{10}$ and $\dot{m}_{20}$, for given values of $w_1$ and $w_2$, are always chosen such that benzene (1) is in a stoichiometric excess relative to nitric acid (2), where
  (iii) in the event of a desired change in the amount of nitric acid (2) supplied to the nitration via the mass flow $\dot{m}_{20}$ from a starting state A defined by a mass flow rate of nitric acid (2) the $(A)=\dot{m}_{20}(A)\cdot w_2(A)$, a mass flow rate of benzene (1) $\dot{m}_1(A)=\dot{m}_{10}(A)\cdot w_1(A)$ selected with regard to (ii) and a mass flow rate of sulfuric acid (3) $\dot{m}_3(A)=\dot{m}_{30}(A)\cdot w_3(A)$,
    to a final state E defined by a mass flow rate of nitric acid (2) the $\dot{m}_2(E)=\dot{m}_{20}(E)\cdot w_2(E)$, a mass flow rate of benzene (1) $\dot{m}_1(E)=\dot{m}_{10}(E)\cdot w_1(E)$ selected with regard to (ii) and a mass flow rate of sulfuric acid (3) $\dot{m}_3(E)=\dot{m}_{30}(E)\cdot w_3(E)$, the mass flow rate than and the proportion by mass $w_2$ are chosen such that the desired value the $\dot{m}_2$ (E) is established, where at least one such change in the amount of nitric acid (2) supplied to the nitration via the mass flow than is conducted, and where this at least one change in the amount of nitric acid (2) supplied to the nitration via the mass flow than is (I) a decrease to a value the $\dot{m}_2$ (E)<$0.95 \cdot \dot{m}_2$ (A) for more than 0.50 hour or (II) an increase to a value the $\dot{m}_2$ (E)>$1.05 \cdot \dot{m}_2$ (A) for more than 0.50 hour, and where, in case (I)

(a) the ratio $\dot{m}_1$ (E)/$\dot{m}_2$ (E) is increased compared to $\dot{m}_1$ (A)/$\dot{m}_2$ (A) such that:
$1.03 \cdot \dot{m}_1$ (A)/$\dot{m}_2$ (A)$\leq \dot{m}_1$ (E)/$\dot{m}_2$ (E)$\leq 1.50 \cdot \dot{m}_1$ (A)/$\dot{m}_2$ (A), especially
$1.05 \cdot \dot{m}_1$ (A)/$\dot{m}_2$ (A)$\leq \dot{m}_1$ (E)/$\dot{m}_2$ (E)$\leq 1.50 \cdot \dot{m}_1$ (A)/$\dot{m}_2$ (A)
and the ratio $\dot{m}_2$ (E)/$\dot{m}_3$ (E) is altered to a maximum degree compared to the ratio $\dot{m}_2$ (A)/$\dot{m}_3$ (A) such that:
$0.98 \cdot \dot{m}_2$ (A)/$\dot{m}_3$ (A)$\leq \dot{m}_2$ (E)/$\dot{m}_3$ (E)$\leq 1.02 \cdot \dot{m}_2$ (A)/$\dot{m}_3$ (A)
or (b) the ratio $\dot{m}_2$ (E)/$\dot{m}_3$ (E) is decreased compared to the ratio $\dot{m}_2$ (A)/$\dot{m}_3$ (A) such that:
$0.45 \cdot \dot{m}_2$ (A)/$\dot{m}_3$ (A)$\leq \dot{m}_2$ (E)/$\dot{m}_3$ (E)$\leq 0.97 \cdot \dot{m}_2$ (A)/$\dot{m}_3$ (A), especially
$0.45 \cdot \dot{m}_2$ (A)/$\dot{m}_3$ (A)$\leq \dot{m}_2$ (E)/$\dot{m}_3$ (E)$\leq 0.95 \cdot \dot{m}_2$ (A)/$\dot{m}_3$ (A)
and the ratio $\dot{m}_1$ (E)/$\dot{m}_2$ (E) is altered to a maximum degree compared to the ratio $\dot{m}_1$ (A)/$\dot{m}_2$ (A) such that:
$0.98 \cdot \dot{m}_1$ (A)/$\dot{m}_2$ (A)$\leq \dot{m}_1$ (E)/$\dot{m}_2$ (E)$\leq 1.02 \cdot \dot{m}_1$ (A)/$\dot{m}_2$ (A)
or (c) the ratio $\dot{m}_1$ (E)/$\dot{m}_2$ (E) is increased compared to $\dot{m}_1$ (A)/$\dot{m}_2$ (A) such that:
$1.03 \cdot \dot{m}_1$ (A)/$\dot{m}_2$ (A)$\leq \dot{m}_1$ (E)/$\dot{m}_2$ (E)$\leq 1.50 \cdot \dot{m}_1$ (A)/$\dot{m}_2$ (A), especially
$1.05 \cdot \dot{m}_1$ (A)/$\dot{m}_2$ (A)$\leq \dot{m}_1$ (E)/$\dot{m}_2$ (E)$\leq 1.50 \cdot \dot{m}_1$ (A)/$\dot{m}_2$ (A)
and the ratio $\dot{m}_2$ (E)/$\dot{m}_3$ (E) is decreased compared to the ratio $\dot{m}_2$ (A)/$\dot{m}_3$ (A) such that:
$0.45 \cdot \dot{m}_2$ (A)/$\dot{m}_3$ (A)$\leq \dot{m}_2$ (E)/$\dot{m}_3$ (E)$\leq 0.97 \cdot \dot{m}_2$ (A)/$\dot{m}_3$ (A), especially
$0.45 \cdot \dot{m}_2$ (A)/$\dot{m}_3$ (A)$\leq \dot{m}_2$ (E)/$\dot{m}_3$ (E)$\leq 0.95 \cdot \dot{m}_2$ (A)/$\dot{m}_3$ (A);

and in case (II)

(a) the ratio $\dot{m}_1$ (E)/$\dot{m}_2$ (E) is decreased compared to $\dot{m}_1$ (A)/$\dot{m}_2$ (A) such that:
$0.45 \cdot \dot{m}_1$ (A)/$\dot{m}_2$ (A)$\leq \dot{m}_1$ (E)/$\dot{m}_2$ (E)$\leq 0.97 \cdot \dot{m}_1$ (A)/$\dot{m}_2$ (A), especially
$0.45 \cdot \dot{m}_1$ (A)/$\dot{m}_2$ (A)$\leq \dot{m}_1$ (E)/$\dot{m}_2$ (E)$\leq 0.95 \cdot \dot{m}_1$ (A)/$\dot{m}_2$ (A)
and the ratio $\dot{m}_2$ (E)/$\dot{m}_3$ (E) is altered to a maximum degree compared to the ratio $\dot{m}_2$ (A)/$\dot{m}_3$ (A) such that:
$0.98 \cdot \dot{m}_2$ (A)/$\dot{m}_3$ (A)$\leq \dot{m}_2$ (E)/$\dot{m}_3$ (E)$\leq 1.02 \cdot \dot{m}_2$ (A)/$\dot{m}_3$ (A)
or (b) the ratio $\dot{m}_2$ (E)/$\dot{m}_3$ (E) is increased compared to the ratio $\dot{m}_2$ (A)/$\dot{m}_3$ (A) such that:
$1.03 \cdot \dot{m}_2$ (A)/$\dot{m}_3$ (A)$\leq \dot{m}_2$ (E)/$\dot{m}_3$ (E)$\leq 1.50 \cdot \dot{m}_2$ (A)/$\dot{m}_3$ (A), especially
$1.05 \cdot \dot{m}_2$ (A)/$\dot{m}_3$ (A)$\leq \dot{m}_2$ (E)/$\dot{m}_3$ (E)$\leq 1.50 \cdot \dot{m}_2$ (A)/$\dot{m}_3$ (A)
and the ratio $\dot{m}_1$ (E)/$\dot{m}_2$ (E) is altered to a maximum degree compared to the ratio $\dot{m}_1$ (A)/$\dot{m}_2$ (A) such that:
$0.98 \cdot \dot{m}_1$ (A)/$\dot{m}_2$ (A)$\leq \dot{m}_1$ (E)/$\dot{m}_2$ (E)$\leq 1.02 \cdot \dot{m}_1$ (A)/$\dot{m}_2$ (A)
or (c) the ratio $\dot{m}_1$ (E)/$\dot{m}_2$ (E) is decreased compared to $\dot{m}_1$ (A)/$\dot{m}_2$ (A) such that:
$0.45 \cdot \dot{m}_1$ (A)/$\dot{m}_2$ (A)$\leq \dot{m}_1$ (E)/$\dot{m}_2$ (E)$\leq 0.97 \cdot \dot{m}_1$ (A)/$\dot{m}_2$ (A), especially
$0.45 \cdot \dot{m}_1$ (A)/$\dot{m}_2$ (A)$\leq \dot{m}_1$ (E)/$\dot{m}_2$ (E)$\leq 0.95 \cdot \dot{m}_1$ (A)/$\dot{m}_2$ (A)
and the ratio $\dot{m}_2$ (E)/$\dot{m}_3$ (E) is increased compared to the ratio $\dot{m}_2$ (A)/$\dot{m}_3$ (A) such that:
$1.03 \cdot \dot{m}_2$ (A)/$\dot{m}_3$ (A)$\leq \dot{m}_2$ (E)/$\dot{m}_3$ (E)$\leq 1.50 \cdot \dot{m}_2$ (A)/$\dot{m}_3$ (A), especially
$1.05 \cdot \dot{m}_2$ (A)/$\dot{m}_3$ (A)$\leq \dot{m}_2$ (E)/$\dot{m}_3$ (E)$\leq 1.50 \cdot \dot{m}_2$ (A)/$\dot{m}_3$ (A).

Completely surprisingly, it has been found that it is advantageous, in the case of a decrease in load—case (I)—to significantly increase the ratio $\dot{m}_1$ (E)/$\dot{m}_2$ (E) compared to $\dot{m}_1$ (A)/$\dot{m}_2$ (A) and/or to significantly decrease the ratio $\dot{m}_2$ (E)/$\dot{m}_3$ (E) compared to the ratio $\dot{m}_2$ (A)/$\dot{m}_2$ (A), or, in the case of an increase in load—case (II)—to significantly decrease the ratio $\dot{m}_1$ (E)/$\dot{m}_2$ (E) compared to $\dot{m}_1$ (A)/$\dot{m}_2$ (A) and/or to significantly increase the ratio $\dot{m}_2$ (E)/$\dot{m}_2$ (E) compared to the ratio $\dot{m}_2$ (A)/$\dot{m}_2$ (A). If a production cycle comprises multiple changes in load, changes in load later in the course of the production cycle can also be conducted in a different variant than earlier changes in load; for example, a first change in load can be conducted by variant (b) and a later change in load by variant (c).

According to the invention, the nitration is supplied with streams 10, 20 and 30. The nitration is conducted in a suitable reactor. Examples of suitable reactors are elucidated in detail further down. The three streams mentioned are supplied continuously to the nitration reactor with a respective mass flow rate $\dot{m}_i$, reported for example in kg/h. In this case, $\dot{m}_{10}$ and $\dot{m}_{20}$, for given values of $w_1$ and $w_2$, are always chosen such that benzene (1) is in a stoichiometric excess relative to nitric acid (2). In stoichiometric terms, for the introduction of a nitro group into a benzene molecule, one molecule of nitric acid is required. For the nitration of one mole of benzene to nitrobenzene, accordingly, one mole of nitric acid is required in stoichiometric terms. Mass flow rates of products (essentially nitrobenzene, excess benzene and dilute sulfuric acid, i.e. sulfuric acid containing the water of reaction) corresponding to the mass flow rates of starting materials supplied are withdrawn continuously from the nitration reactor.

The proportion by mass $w_i$ of a component i in a stream z denotes the quotient of the mass flow rate of component i and the total mass flow rate of stream z. If, for example, the proportion by mass $w_1$ of benzene is 0.980, the benzene-containing stream 10 consists to an extent of 98.0% by mass of benzene and to an extent of 2.0% by mass of other constituents (for example aliphatic organic compounds from the proportion of recycled benzene ("return benzene") present in a preferred configuration in the benzene stream 10). The proportions by mass $w_2$ and $w_3$ of the nitric acid stream and the sulfuric acid stream 20 and 30 denote the theoretical proportion by mass of $HNO_3$ (2) and $H_2SO_4$ (3) in the respective stream, regardless of the fact that these acids are in fact in dissociated form. If, for example, a 70.0% sulfuric acid is used as stream 30, $w_3=0.700$.

Since benzene (1) is used in excess in accordance with the invention, the yield of nitrobenzene is determined by the throughput (by the load) of nitric acid used, i.e. by the mass flow rate $\dot{m}_2$. The process of the invention comprises at least one change in load, i.e. a change in the mass flow rate $\dot{m}_2$ proceeding from a starting state A with $\dot{m}_2$ (A) to a final state E with $\dot{m}_2$ (E). A change in the amount of nitric acid (2) supplied to the nitration via the mass flow $\dot{m}_{20}$, i.e. a change in the mass flow $\dot{m}_2$ in this context, is a change by more than 5.00% (i.e. $\dot{m}_2$ (E)≤0.95·$\dot{m}_2$ (A) in the event of decreases in load or $\dot{m}_2$ (E)>1.05·$\dot{m}_2$ (A) in the event of increases in load) for a period of more than 0.50 hour, preferably of more than 2.0 hours, more preferably of more than 6.0 hours, even more preferably of more than 12 hours, even more exceptionally preferably of more than 24 hours. Smaller changes or changes over a shorter period of time, for the purposes of this invention, are to be regarded as unintended changes in load as can occur time and again in everyday operation. Preferably, changes in load in the context of the present invention vary within the range defined as follows: 0.40·$\dot{m}_2$ (A)≤$\dot{m}_2$ (E)≤2.50·$\dot{m}_2$ (A), naturally excluding the aforementioned range from 0.95·$\dot{m}_2$ (A) to 1.05·$\dot{m}_2$ (A), since it is not to be regarded as a significant change in load for the purposes of the present invention. The process of the invention may of course also include multiple changes in load, especially first a decrease in load as per case (I) and, at a later juncture, an increase in load as per case (II).

By way of example, a halving of the load (i.e. $\dot{m}_2$ (E)=0.50·$\dot{m}_2$ (A)) proceeding from production at nameplate load shall be considered as follows:

In operation at nameplate load with an appropriate mass flow rate $\dot{m}_2 = \dot{m}_{2,\,name}$, the process of the invention can be conducted as known from the prior art. With known $\dot{m}_2 = \dot{m}_{2,\,name}$, $w_2$ (and hence $\dot{m}_{20}$) and the parameters $w_i$ and $\dot{m}_i$ of streams 10 and 30 are fixed by the person skilled in the art within the scope of his knowledge in the art and taking account of the boundary conditions of the production plant in question. The production plant produces the desired product continuously until, for example owing to a fall in demand, the throughput of nitric acid (2) is to be halved, for example. In the terminology of the present invention, this means a change in the mode of operation proceeding from the starting state A (=production at nameplate load) to a final state E (production at half load). The decrease in load is automatically associated with halving of the nitric acid mass flow rate $\dot{m}_2$ guided into the nitration. In principle, this halving could be achieved by halving $w_2$ and keeping $\dot{m}_{20}$ constant. However, it is preferable, in the change in load, to keep the proportion by mass $w_2$ the same and to vary $\dot{m}_{20}$ (to halve it in the specific example). The same is true of each of the proportions by mass $w_1$ and $w_3$. By contrast with the prior art, it is not simply the case that the mass flow rates $\dot{m}_{10}$ and $\dot{m}_{30}$ are reduced to the same degree as $\dot{m}_{20}$; instead, the ratio $\dot{m}_1$ (E)/$\dot{m}_2$ (E) is significantly increased compared to $\dot{m}_1$ (A)/$\dot{m}_2$ (A) and/or the ratio $\dot{m}_2$ (E)/$\dot{m}_3$ (E) is significantly decreased compared to the ratio $\dot{m}_2$ (A)/$\dot{m}_2$ (A). If just one of the mass ratios mentioned is significantly increased or decreased (abovementioned variants (a) and (b)), the other mass ratio in each case is kept essentially the same. The terms "significantly increase or decrease" and "keep essentially the same" are defined here by the numerical limits listed in the abovementioned variants (a), (b) and (c). If, as is preferable for all embodiments in accordance with the invention, all proportions by mass $w_i$ are kept constant, this course of action is equivalent to the statement that the ratio $\dot{m}_{10}$ (E)/$\dot{m}_{20}$ (E) is significantly increased compared to $\dot{m}_{10}$ (A)/$\dot{m}_{20}$ (A) and/or the ratio $\dot{m}_{20}$ (E)/$\dot{m}_{30}$ (E) is significantly decreased compared to the ratio $\dot{m}_{20}$ (A)/$\dot{m}_{30}$ (A). According to the invention, it is preferable for all embodiments to conduct a decrease in load as per variant (b).

After a certain production period at half-load, the production is then to be increased again to nameplate load (or a lower value, for example three-quarter load, if the demand for the product has not yet reached the original value again). In the terminology of the present invention, production at half-load is now the (new) starting state and production at nameplate load (or at a lower value, for example three-quarter load) is the final state. According to the invention, therefore, the ratio $\dot{m}_1$ (E)/$\dot{m}_2$ (E) is significantly decreased compared to $\dot{m}_1$ (A)/$\dot{m}_2$ (A) and/or the ratio $\dot{m}_2$ (E)/$\dot{m}_2$ (E) is significantly increased compared to the ratio $\dot{m}_2$ (A)/$\dot{m}_2$ (A). According to the invention, it is preferable for all embodiments to conduct an increase in load as per variant (b). The other statements made above are correspondingly applicable. Preferably, the conditions as before the first change in load are reestablished.

There follows firstly a brief summary of various possible embodiments of the invention:

In a first embodiment of the invention, which may be combined with all other embodiments, the nitration of benzene to nitrobenzene is operated adiabatically.

In a second embodiment of the invention, which is a particular configuration of the first embodiment, the nitration of benzene to nitrobenzene comprises the following steps:

(I) nitrating benzene with nitric acid and sulfuric acid to form nitrobenzene in a reactor, with introduction of a benzene-containing stream 10 with a mass flow rate of $\dot{m}_{10}$, a nitric acid-containing stream 20 with a mass flow rate of $\dot{m}_{20}$ and a sulfuric acid-containing stream 30 with a mass flow rate of $\dot{m}_{30}$ into the reactor;

(II) separating the phases of the reaction mixture from step (I) in a phase separation apparatus into an aqueous, sulfuric acid-containing phase and an organic nitrobenzene-containing phase;

(III) concentrating the aqueous phase obtained in step (II) by evaporating water in an evaporation apparatus to give an aqueous sulfuric acid-containing phase having elevated sulfuric acid concentration, with recycling of the concentrated sulfuric acid-containing aqueous phase into step (I) and use thereof as a constituent of the sulfuric acid-containing stream 30;

(IV) washing, in at least two stages, the organic, nitrobenzene-containing phase obtained in step (II) and separating the aqueous phase off after each stage;

(V) distilling, preferably rectifying, the organic, nitrobenzene-containing phase obtained in the last stage of step (IV) with removal of unconverted benzene which is recycled into step (I) and used as a constituent of the benzene-containing stream 10.

In a third embodiment of the invention, which is a particular configuration of the second embodiment, step (V) is followed by:

(VI) working up the wastewater from the first wash stage of step (IV), comprising cleaning this wastewater in an apparatus for distillation or stripping, (VII) working up the wastewater from the second wash stage of step (IV), comprising cleaning this wastewater in an apparatus for distillation or stripping, where an apparatus for thermal pressure decomposition may be connected up- and/or downstream of the apparatus for distillation or stripping.

In a fourth embodiment of the invention, which is a particular configuration of the second and third embodiments, step (IV) comprises:

(IVa) washing the organic nitrobenzene-containing phase obtained in step (II) in at least one wash, then separating the phases into an aqueous phase and an organic nitrobenzene-containing phase (first wash stage);

(IVb) washing the organic phase obtained in step (IVa) in at least one alkaline wash with an aqueous solution of a base preferably selected from the group consisting of sodium hydroxide, sodium carbonate and sodium hydrogencarbonate, then separating the phases into an aqueous phase and an organic nitrobenzene-containing phase (second wash stage);

(IVc) washing the organic phase obtained in step (IVb) in at least one neutral wash, preferably two to four neutral washes, more preferably two to three neutral washes, most preferably two neutral washes, with water, then separating the phases into an aqueous phase and an organic nitrobenzene-containing organic phase (third wash stage).

In a fifth embodiment of the invention, which can be combined with all other embodiments, the ratio $\dot{m}_1$ (A)/$\dot{m}_2$ (A) is in the range from 1.26 to 1.74, preferably in the range from 1.28 to 1.61, more preferably in the range from 1.29 to 1.55 and most preferably in the range from 1.30 to 1.49.

In a sixth embodiment of the invention, which can be combined with all other embodiments, the change in load is effected within the range defined as follows: 0.40·$\dot{m}_2$ (A)≤$\dot{m}_2$ (E)≤2.50·$\dot{m}_2$ (A), excluding the range from 0.95·$\dot{m}_2$ (A) to 1.05·$\dot{m}_2$ (A) for $\dot{m}_2$ (E), since it is not to be regarded as a significant change in load for the purposes of the present invention.

In a seventh embodiment of the invention, which is a particular configuration of the sixth embodiment, the change in load is conducted by variant (a), where, in case (I) (i.e. $\dot{m}_2$ (E)<0.95·$\dot{m}_2$ (A)), the following relationships are applicable:

when $\dot{m}_2$ (E) is in the range from 0.80·$\dot{m}_2$ (A) to <0.95·$\dot{m}_2$ (A), $\dot{m}_1$ (E)/$\dot{m}_2$ (E) is adjusted to a value in the range from 1.03·$\dot{m}_1$ (A)/$\dot{m}_2$ (A) to 1.20·$\dot{m}_1$ (A)/$\dot{m}_2$ (A), especially 1.05·$\dot{m}_1$ (A)/$\dot{m}_2$ (A) to 1.20·$\dot{m}_1$ (A)/$\dot{m}_2$ (A);

when $\dot{m}_2$ (E) is in the range from 0.65·$\dot{m}_2$ (A) to <0.80·$\dot{m}_2$ (A), $\dot{m}_1$ (E)/$\dot{m}_2$ (E) is adjusted to a value in the range from >1.20·$\dot{m}_1$ (A)/$\dot{m}_2$ (A) to 1.40·$\dot{m}_1$ (A)/$\dot{m}_2$ (A);
and when $\dot{m}_2$ (E) is in the range from 0.40·$\dot{m}_2$ (A) to <0.65·$\dot{m}_2$ (A), $\dot{m}_1$ (E)/$\dot{m}_2$ (E) is adjusted to a value in the range from >1.40·$\dot{m}_1$ (A)/$\dot{m}_2$ (A) to 1.50·$\dot{m}_1$ (A)/$\dot{m}_2$ (A);

where, in addition, in case (II) (i.e. $\dot{m}_2$ (E)>1.05·$\dot{m}_2$ (A)), the following relationships are applicable:

when $\dot{m}_2$ (E) is in the range from >1.05·$\dot{m}_2$ (A) to 1.50·$\dot{m}_2$ (A), $\dot{m}_1$ (E)/$\dot{m}_2$ (E) is adjusted to a value in the range from 0.75·$\dot{m}_1$ (A)/$\dot{m}_2$ (A) to 0.97·$\dot{m}_1$ (A)/$\dot{m}_2$ (A), especially 0.75·$\dot{m}_1$ (A)/$\dot{m}_2$ (A) to 0.95·$\dot{m}_1$ (A)/$\dot{m}_2$ (A);

when $\dot{m}_2$ (E) is in the range from >1.50·$\dot{m}_2$ (A) to 2.00·$\dot{m}_2$ (A), $\dot{m}_1$ (E)/$\dot{m}_2$ (E) is adjusted to a value in the range from 0.55·$\dot{m}_1$ (A)/$\dot{m}_2$ (A) to <0.75·$\dot{m}_1$ (A)/$\dot{m}_2$ (A);
and when $\dot{m}_2$ (E) is in the range from >2.00·$\dot{m}_2$ (A) to 2.50·$\dot{m}_2$ (A), $\dot{m}_1$ (E)/$\dot{m}_2$ (E) is adjusted to a value in the range from 0.45·$\dot{m}_1$ (A)/$\dot{m}_2$ (A) to <0.55·$\dot{m}_1$ (A)/$\dot{m}_2$ (A).

In an eighth embodiment of the invention, which is a particular configuration of the sixth embodiment, the change in load is conducted by variant (b), where, in case (I) (i.e. $\dot{m}_2$ (E)≤0.95·$\dot{m}_2$ (A)), the following relationships are applicable:

when $\dot{m}_2$ (E) is in the range from 0.80·$\dot{m}_2$ (A) to <0.95·$\dot{m}_2$ (A), $\dot{m}_2$ (E)/$\dot{m}_3$ (E) is adjusted to a value in the range from 0.80·$\dot{m}_2$ (A)/$\dot{m}_3$ (A) to 0.97·$\dot{m}_2$ (A)/$\dot{m}_3$ (A), especially 0.80·$\dot{m}_2$ (A)/$\dot{m}_3$ (A) to 0.95·$\dot{m}_2$ (A)/$\dot{m}_3$ (A);

when $\dot{m}_2$ (E) is in the range from 0.65·$\dot{m}_2$ (A) to <0.80·$\dot{m}_2$ (A), $\dot{m}_2$ (E)/$\dot{m}_3$ (E) is adjusted to a value in the range from 0.65·$\dot{m}_2$ (A)/$\dot{m}_3$ (A) to <0.80·$\dot{m}_2$ (A)/$\dot{m}_3$ (A);
and when $\dot{m}_2$ (E) is in the range from 0.40·$\dot{m}_2$ (A) to <0.65·$\dot{m}_2$ (A), $\dot{m}_2$ (E)/$\dot{m}_3$ (E) is adjusted to a value in the range from 0.40·$\dot{m}_2$ (A)/$\dot{m}_3$ (A) to <0.65·$\dot{m}_2$ (A)/$\dot{m}_3$ (A);

where, in addition, in case (II) (i.e. $\dot{m}_2$ (E)>1.05·$\dot{m}_2$ (A)), the following relationships are applicable:

when $\dot{m}_2$ (E) is in the range from >1.05·$\dot{m}_2$ (A) to 1.50·$\dot{m}_2$ (A), $\dot{m}_2$ (E)/$\dot{m}_3$ (E) is adjusted to a value in the range from 1.03·$\dot{m}_2$ (A)/$\dot{m}_3$ (A) to 1.50·$\dot{m}_2$ (A)/$\dot{m}_3$ (A), especially 1.05·$\dot{m}_2$ (A)/$\dot{m}_3$ (A) to 1.50·$\dot{m}_2$ (A)/$\dot{m}_3$ (A);

when $\dot{m}_2$ (E) is in the range from >1.50·$\dot{m}_2$ (A) to 2.00·$\dot{m}_2$ (A), $\dot{m}_2$ (E)/$\dot{m}_3$ (E) is adjusted to a value in the range from >1.50·$\dot{m}_2$ (A)/$\dot{m}_3$ (A) to 2.00·$\dot{m}_2$ (A)/$\dot{m}_3$ (A);
and when $\dot{m}_2$ (E) is in the range from >2.00·$\dot{m}_2$ (A) to 2.50·$\dot{m}_2$ (A), $\dot{m}_2$ (E)/$\dot{m}_3$ (E) is adjusted to a value in the range from >2.00·$\dot{m}_2$ (A)/$\dot{m}_3$ (A) to 2.50·$\dot{m}_2$ (A)/$\dot{m}_3$ (A).

In a ninth embodiment of the invention, which is a particular configuration of the sixth embodiment, the change in load is conducted by variant (c), where, in case (I) (i.e. $\dot{m}_2$ (E)<0.95·$\dot{m}_2$ (A)), the following relationships are applicable:

when $\dot{m}_2$ (E) is in the range from 0.80·$\dot{m}_2$ (A) to <0.95·$\dot{m}_2$ (A), $\dot{m}_1$ (E)/$\dot{m}_2$ (E) is adjusted to a value in the range from 1.03·$\dot{m}_1$ (A)/$\dot{m}_2$ (A) to 1.20·$\dot{m}_1$ (A)/$\dot{m}_2$ (A), especially 1.05·$\dot{m}_1$ (A)/$\dot{m}_2$ (A) to 1.20·$\dot{m}_1$ (A)/$\dot{m}_2$ (A), and $\dot{m}_2$ (E)/$\dot{m}_3$ (E) to a value in the range from 0.80·$\dot{m}_2$ (A)/$\dot{m}_3$ (A) to 0.97·$\dot{m}_2$ (A)/$\dot{m}_3$ (A), especially 0.80·$\dot{m}_2$ (A)/$\dot{m}_3$ (A) to 0.95·$\dot{m}_2$ (A)/$\dot{m}_3$ (A);

when $\dot{m}_2$ (E) is in the range from 0.65·$\dot{m}_2$ (A) to <0.80·$\dot{m}_2$ (A), $\dot{m}_1$ (E)/$\dot{m}_2$ (E) is adjusted to a value in the range from >1.20·$\dot{m}_1$ (A)/$\dot{m}_2$ (A) to 1.40·$\dot{m}_1$ (A)/$\dot{m}_2$ (A) and $\dot{m}_2$ (E)/$\dot{m}_3$ (E) to a value in the range from 0.65·$\dot{m}_2$ (A)/$\dot{m}_3$ (A) to <0.80·$\dot{m}_2$ (A)/$\dot{m}_3$ (A);
and when $\dot{m}_2$ (E) is in the range from to 0.40·$\dot{m}_2$ (A) to <0.65·$\dot{m}_2$ (A), $\dot{m}_1$ (E)/$\dot{m}_2$ (E) is adjusted to a value in the range from >1.40·$\dot{m}_1$ (A)/$\dot{m}_2$ (A) to 1.50·$\dot{m}_1$ (A)/$\dot{m}_2$ (A) and $\dot{m}_2$ (E)/$\dot{m}_3$ (E) to a value in the range from 0.40·$\dot{m}_2$ (A)/$\dot{m}_3$ (A) to <0.65·$\dot{m}_2$ (A)/$\dot{m}_3$ (A);

where, in addition, in case (II) (i.e. $\dot{m}_2$ (E)>1.05·$\dot{m}_2$ (A)), the following relationships are applicable:

when $\dot{m}_2$ (E) is in the range from >1.05·$\dot{m}_2$ (A) to 1.50·$\dot{m}_2$ (A), $\dot{m}_1$ (E)/$\dot{m}_2$ (E) is adjusted to a value in the range from 0.75·$\dot{m}_1$ (A)/$\dot{m}_2$ (A) to 0.97·$\dot{m}_1$ (A)/$\dot{m}_2$ (A), especially 0.75·$\dot{m}_1$ (A)/$\dot{m}_2$ (A) to 0.95·$\dot{m}_1$ (A)/$\dot{m}_2$ (A), and $\dot{m}_2$ (E)/$\dot{m}_3$ (E) to a value in the range from 1.03·$\dot{m}_2$ (A)/$\dot{m}_3$ (A) to 1.50·$\dot{m}_2$ (A)/$\dot{m}_3$ (A), especially 1.05·$\dot{m}_2$ (A)/$\dot{m}_3$ (A) to 1.50·$\dot{m}_2$ (A)/$\dot{m}_3$ (A);

when $\dot{m}_2$ (E) is in the range from >1.50·$\dot{m}_2$ (A) to 2.00·$\dot{m}_2$ (A), $\dot{m}_1$ (E)/$\dot{m}_2$ (E) is adjusted to a value in the range from 0.55·$\dot{m}_1$ (A)/$\dot{m}_2$ (A) to <0.75·$\dot{m}_1$ (A)/$\dot{m}_2$ (A) and $\dot{m}_2$ (E)/$\dot{m}_3$ (E) to a value in the range from >1.50·$\dot{m}_2$ (A)/$\dot{m}_3$ (A) to 2.00·$\dot{m}_2$ (A)/$\dot{m}_3$ (A);
and when $\dot{m}_2$ (E) is in the range from >2.00·$\dot{m}_2$ (A) to 2.50·$\dot{m}_2$ (A), $\dot{m}_1$ (E)/$\dot{m}_2$ (E) is adjusted to a value in the range from 0.45·$\dot{m}_1$ (A)/$\dot{m}_2$ (A) to <0.55·$\dot{m}_1$ (A)/$\dot{m}_2$ (A) and $\dot{m}_2$ (E)/$\dot{m}_3$ (E) to a value in the range from >2.00·$\dot{m}_2$ (A)/$\dot{m}_3$ (A) to 2.50·$\dot{m}_2$ (A)/$\dot{m}_3$ (A).

If a production cycle for preparation of nitrobenzene comprises multiple changes in load in the context of the present invention, the seventh, eighth and ninth embodiments may also be combined.

For example, the load can first be reduced proceeding from nameplate load in the seventh embodiment (case (I)) to half-load, increased at a later juncture as per the eighth embodiment (case (II)) to three-quarter load, and brought back at a still later juncture as per the ninth embodiment (case (III)) to nameplate load.

In a tenth embodiment of the invention, which is a particular configuration of the eighth and ninth embodiments: $0.98 \cdot \dot{m}_3$ (A)$\leq \dot{m}_3$ (E)$\leq 1.02 \cdot \dot{m}_3$ (A), especially $\dot{m}_3$ (A)=$\dot{m}_3$ (E).

In an eleventh embodiment of the invention, which may be combined with all other embodiments, $w_1$ (A)=$w_1$ (E).

In a twelfth embodiment of the invention, which may be combined with all other embodiments, $w_2$ (A)=$w_2$ (E).

In a thirteenth embodiment of the invention, which may be combined with all other embodiments, $w_3$ (A)=$w_3$ (E).

In a fourteenth embodiment of the invention, which may be combined with all other embodiments, $w_1$ (A)=$w_1$ (E), $w_2$ (A)=$w_2$ (E) and $w_3$ (A)=$w_3$ (E).

In a fifteenth embodiment of the invention, which may be combined with all other embodiments, the process comprises a decrease in the amount of nitric acid (2) supplied to the nitration via the mass flow $\dot{m}_{20}$ as per case (I), wherein this reduction is conducted as per variant (b).

In a sixteenth embodiment of the invention, which may be combined with all other embodiments, especially with the fifteenth embodiment, the process comprises an increase in the amount of nitric acid (2) supplied to the nitration via the mass flow $\dot{m}_{20}$ as per case (II), wherein this increase is conducted as per variant (b), especially after a preceding decrease in the amount of nitric acid (2) supplied to the nitration via the mass flow $\dot{m}_{20}$ as per the fifteenth embodiment.

In a seventeenth embodiment of the invention, which may be combined with all other embodiments,
in case (I)
(a) the ratio $\dot{m}_1$ (E)/$\dot{m}_2$ (E) is increased compared to $\dot{m}_1$ (A)/$\dot{m}_2$ (A) such that:
$1.05 \cdot \dot{m}_1$ (A)/$\dot{m}_2$ (A)$\leq \dot{m}_1$ (E)/$\dot{m}_2$ (E)$\leq 1.50 \cdot \dot{m}_1$ (A)/$\dot{m}_2$ (A)
and the ratio $\dot{m}_2$ (E)/$\dot{m}_3$ (E) is altered to a maximum degree compared to the ratio $\dot{m}_2$ (A)/$\dot{m}_3$ (A) such that:
$0.98 \cdot \dot{m}_2$ (A)/$\dot{m}_3$ (A)$\leq \dot{m}_2$ (E)/$\dot{m}_3$ (E)$\leq 1.02 \cdot \dot{m}_2$ (A)/$\dot{m}_3$ (A)
or
(b) the ratio $\dot{m}_2$ (E)/$\dot{m}_3$ (E) is decreased compared to the ratio $\dot{m}_2$ (A)/$\dot{m}_3$ (A) such that:
$0.45 \cdot \dot{m}_2$ (A)/$\dot{m}_3$ (A)$\leq \dot{m}_2$ (E)/$\dot{m}_3$ (E)$\leq 0.95 \cdot \dot{m}_2$ (A)/$\dot{m}_3$ (A)
and the ratio $\dot{m}_1$ (E)/$\dot{m}_2$ (E) is altered to a maximum degree compared to the ratio $\dot{m}_1$ (A)/$\dot{m}_2$ (A) such that:
$0.98 \cdot \dot{m}_1$ (A)/$\dot{m}_2$ (A)$\leq \dot{m}_1$ (E)/$\dot{m}_2$ (E)$\leq 1.02 \cdot \dot{m}_1$ (A)/$\dot{m}_2$ (A)
or
(c) the ratio $\dot{m}_1$ (E)/$\dot{m}_2$ (E) is increased compared to $\dot{m}_1$ (A)/$\dot{m}_2$ (A) such that:
$1.05 \cdot \dot{m}_1$ (A)/$\dot{m}_2$ (A)$\leq \dot{m}_1$ (E)/$\dot{m}_2$ (E)$\leq 1.50 \cdot \dot{m}_1$ (A)/$\dot{m}_2$ (A)
and the ratio $\dot{m}_2$ (E)/$\dot{m}_3$ (E) is decreased compared to the ratio $\dot{m}_2$ (A)/$\dot{m}_3$ (A) such that:
$0.45 \cdot \dot{m}_2$ (A)/$\dot{m}_3$ (A)$\leq \dot{m}_2$ (E)/$\dot{m}_3$ (E)$\leq 0.95 \cdot \dot{m}_2$ (A)/$\dot{m}_3$ (A);
and
in case (II)
(a) the ratio $\dot{m}_1$ (E)/$\dot{m}_2$ (E) is decreased compared to $\dot{m}_1$ (A)/$\dot{m}_2$ (A) such that:
$0.45 \cdot \dot{m}_1$ (A)/$\dot{m}_2$ (A)$\leq \dot{m}_1$ (E)/$\dot{m}_2$ (E)$\leq 0.95 \cdot \dot{m}_1$ (A)/$\dot{m}_2$ (A)
and the ratio $\dot{m}_2$ (E)/$\dot{m}_3$ (E) is altered to a maximum degree compared to the ratio $\dot{m}_2$ (A)/$\dot{m}_3$ (A) such that:
$0.98 \cdot \dot{m}_2$ (A)/$\dot{m}_3$ (A)$\leq \dot{m}_2$ (E)/$\dot{m}_3$ (E)$\leq 1.02 \cdot \dot{m}_2$ (A)/$\dot{m}_3$ (A)
or
(b) the ratio $\dot{m}_2$ (E)/$\dot{m}_3$ (E) is increased compared to the ratio $\dot{m}_2$ (A)/$\dot{m}_3$ (A) such that:
$1.05 \cdot \dot{m}_2$ (A)/$\dot{m}_3$ (A)$\leq \dot{m}_2$ (E)/$\dot{m}_3$ (E)$\leq 1.50 \cdot \dot{m}_2$ (A)/$\dot{m}_3$ (A)
and the ratio $\dot{m}_1$ (E)/$\dot{m}_2$ (E) is altered to a maximum degree compared to the ratio $\dot{m}_1$ (A)/$\dot{m}_2$ (A) such that:
$0.98 \cdot \dot{m}_1$ (A)/$\dot{m}_2$ (A)$\leq \dot{m}_1$ (E)/$\dot{m}_2$ (E)$\leq 1.02 \cdot \dot{m}_1$ (A)/$\dot{m}_2$ (A)
or
(c) the ratio $\dot{m}_1$ (E)/$\dot{m}_2$ (E) is decreased compared to $\dot{m}_1$ (A)/$\dot{m}_2$ (A) such that:
$0.45 \cdot \dot{m}_1$ (A)/$\dot{m}_2$ (A)$\leq \dot{m}_1$ (E)/$\dot{m}_2$ (E)$\leq 0.95 \cdot \dot{m}_1$ (A)/$\dot{m}_2$ (A)
and the ratio $\dot{m}_2$ (E)/$\dot{m}_3$ (E) is increased compared to the ratio $\dot{m}_2$ (A)/$\dot{m}_3$ (A) such that:
$1.05 \cdot \dot{m}_2$ (A)/$\dot{m}_3$ (A)$\leq \dot{m}_2$ (E)/$\dot{m}_3$ (E)$\leq 1.50 \cdot \dot{m}_2$ (A)/$\dot{m}_3$ (A).

The embodiments briefly outlined above and further possible configurations of the invention are elucidated in detail hereinafter. Various embodiments are combinable with one another as desired unless the opposite is apparent to the person skilled in the art from the context.

The stream 10 containing benzene (1) with a proportion by mass of benzene (1) of $w_1$ consists essentially, i.e. preferably to an extent of at least 95.0% by mass, more preferably to an extent of at least 98.0% by mass, based on the total mass of stream 10, of benzene; in other words, the proportion by mass of benzene (1) in stream 10, $w_1$, is preferably at least 0.950, more preferably at least 0.980. Since benzene, in accordance with the invention, is used in excess (cf. (ii)), there always remains a proportion of unconverted benzene, which is preferably, optionally after purification, recycled into the nitration and becomes part of stream 10. The impurities present in this recycled benzene stream, together with any impurities present in the freshly supplied benzene, make up the remaining portion of stream 10. Likewise remaining after the reaction is sulfuric acid, which has been merely diluted but not chemically consumed. Preferably, the sulfuric acid is concentrated and, optionally after purification, recycled into the nitration and used as part of stream 30.

In one embodiment of the present invention, in the starting state, in continuous operation, preference is given to maintaining a stoichiometric excess of benzene in the range from 2.00% to 40.0%, more preferably in the range from 3.00% to 30.0%, even more preferably in the range from 4.00% to 25.0% and very exceptionally preferably in the range from 5.00% to 20.00%. This corresponds to a ratio $\dot{m}_1$ (A)/$\dot{m}_2$ (A) in the range from preferably 1.26 to 1.74, more preferably 1.28 to 1.61, even more preferably 1.29 to 1.55 and very exceptionally preferably in the range from 1.30 to 1.49. (Higher excesses of benzene than 20.00% (for instance 45.00%, 40.00% or 30.00%) are generally not desirable but are of course possible.) This embodiment is preferentially suitable for a process regime with decreased load (especially for operation at nameplate load in the starting state and part-load in the final state). In any case, it is preferable to keep the stoichiometric excess of benzene as small as possible (but not too low either, because there can otherwise be an increased degree of formation of dinitrobenzene). As a result, firstly, the formation of unwanted by-products (especially solid deposits) is reduced and, secondly, energy is saved since less benzene has to be recovered. It is therefore especially preferable, in the starting state (especially production at nameplate load), to set the ratio $\dot{m}_1$ (A)/$\dot{m}_2$ (A) to a value in the range from 1.26 to 1.49 (in accordance with a stoichiometric excess of benzene in the range from 2.00% to 20.00%).

If the nitric acid load is then to be decreased, this is done in variant (A), in which $\dot{m}_1$ (E)/$\dot{m}_2$ (E) is increased by comparison with $\dot{m}_1$ (A)/$\dot{m}_2$ (A). The extent of the increase depends on the extent of the change in load. Preferably:

| Extent of the change in load: $\dot{m}_2(E)$ is in the range | Extent of the increase: $\dot{m}_1(E)/\dot{m}_2(E)$ is in the range |
|---|---|
| from $0.80 \cdot \dot{m}_2(A)$ to $<0.95 \cdot \dot{m}_2(A)$ | from $1.03 \cdot \dot{m}_1(A)/\dot{m}_2(A)$ to $1.20 \cdot \dot{m}_1(A)/\dot{m}_2(A)$, especially $1.05 \cdot \dot{m}_1(A)/\dot{m}_2(A)$ to $1.20 \cdot \dot{m}_1(A)/\dot{m}_2(A)$ |
| from $0.65 \cdot \dot{m}_2(A)$ to $<0.80 \cdot \dot{m}_2(A)$ | from $>1.20 \cdot \dot{m}_1(A)/\dot{m}_2(A)$ to $1.40 \cdot \dot{m}_1(A)/\dot{m}_2(A)$ |
| from $0.40 \cdot \dot{m}_2(A)$ to $<0.65 \cdot \dot{m}_2(A)$ | from $>1.40 \cdot \dot{m}_1(A)/\dot{m}_2(A)$ to $1.50 \cdot \dot{m}_1(A)/\dot{m}_2(A)$ |

If, in variant (a), the nitric acid load is to be increased from an operating state with lower than nameplate load (part-load) (especially back to nameplate mode), according to the invention, the ratio $\dot{m}_1/\dot{m}_2$ is decreased. The extent of the decrease depends on the extent of the change in load. Preferably:

| Extent of the change in load: $\dot{m}_2(E)$ is in the range | Extent of the decrease: $\dot{m}_1(E)/\dot{m}_2(E)$ is in the range |
|---|---|
| from $>1.05 \cdot \dot{m}_2(A)$ to $1.50 \cdot \dot{m}_2(A)$ | from $0.75 \cdot \dot{m}_1(A)/\dot{m}_2(A)$ to $0.97 \cdot \dot{m}_1(A)/\dot{m}_2(A)$, especially $0.75 \cdot \dot{m}_1(A)/\dot{m}_2(A)$ to $0.95 \cdot \dot{m}_1(A)/\dot{m}_2(A)$ |
| from $>1.50 \cdot \dot{m}_2(A)$ to $2.00 \cdot \dot{m}_2(A)$ | from $0.55 \cdot \dot{m}_1(A)/\dot{m}_2(A)$ to $<0.75 \cdot \dot{m}_1(A)/\dot{m}_2(A)$ |
| from $>2.00 \cdot \dot{m}_2(A)$ to $2.50 \cdot \dot{m}_2(A)$ | from $0.45 \cdot \dot{m}_1(A)/\dot{m}_2(A)$ to $<0.55 \cdot \dot{m}_1(A)/\dot{m}_2(A)$ |

It should be noted here that starting state and final state have been transposed compared to the original situation of the decrease in load proceeding from nameplate load.

When the nitric acid load is to be decreased proceeding from a starting state having a preferred stoichiometric excess of benzene in the range from 2.00% to 40.0%, more preferably in the range from 3.00% to 30.0%, even more preferably in the range from 4.00% to 25.0% and very exceptionally preferably in the range from 5.00% to 20.00% (corresponding to a ratio $\dot{m}_1(A)/\dot{m}_2(A)$ in the range from preferably 1.26 to 1.74, more preferably 1.28 to 1.61, even more preferably 1.29 to 1.55 and very exceptionally preferably in the range from 1.30 to 1.49; see above), this can also be done in variant (b) in which the ratio $\dot{m}_2(E)/\dot{m}_3(E)$ is decreased compared to $\dot{m}_2(A)/\dot{m}_3(A)$. Preferably:

| Extent of the change in load: $\dot{m}_2(E)$ is in the range | Extent of the decrease: $\dot{m}_2(E)/\dot{m}_3(E)$ is in the range |
|---|---|
| from $0.80 \cdot \dot{m}_2(A)$ to $<0.95 \cdot \dot{m}_2(A)$ | from $0.80 \cdot \dot{m}_2(A)/\dot{m}_3(A)$ to $0.97 \cdot \dot{m}_2(A)/\dot{m}_3(A)$, especially $0.80 \cdot \dot{m}_2(A)/\dot{m}_3(A)$ to $0.95 \cdot \dot{m}_2(A)/\dot{m}_3(A)$ |
| from $0.65 \cdot \dot{m}_2(A)$ to $<0.80 \cdot \dot{m}_2(A)$ | from $0.65 \cdot \dot{m}_2(A)/\dot{m}_3(A)$ to $<0.80 \cdot \dot{m}_2(A)/\dot{m}_3(A)$ |
| from $0.40 \cdot \dot{m}_2(A)$ to $<0.65 \cdot \dot{m}_2(A)$ | from $0.40 \cdot \dot{m}_2(A)/\dot{m}_3(A)$ to $<0.65 \cdot \dot{m}_2(A)/\dot{m}_3(A)$ |

In variant (b), it is particularly preferable to keep the absolute value $\dot{m}_3$ constant or at least essentially (±2.0%) constant (i.e., more preferably, $0.98 \cdot \dot{m}_3(A) \leq \dot{m}_3(E) \leq 1.02 \cdot \dot{m}_3(A)$). If, as is preferred, $w_3$ is also kept constant, this means that the mass flow rate $\dot{m}_{30}$ is preferably maintained or essentially (±2.0%) maintained. If $\dot{m}_3$ is kept the same, the percentage decrease in load corresponds to the percentage decrease in the ratio $\dot{m}_2/\dot{m}_3$. In the event of a decrease in load to, for example, 75% of the starting value (i.e. $\dot{m}_2(E)=0.75 \cdot \dot{m}_2(A)$), the ratio $\dot{m}_2/\dot{m}_3$ is then likewise decreased to 75% of the starting value (i.e. $\dot{m}_2(E)/\dot{m}_3(E)=0.75 \cdot \dot{m}_2(A)/\dot{m}_3(A)$).

If, in variant (b), the nitric acid load is to be increased from an operating state with lower than nameplate load (part-load) (especially back to nameplate load), according to the invention, the ratio $\dot{m}_2/\dot{m}_3$ is increased. Preferably:

| Extent of the change in load: $\dot{m}_2(E)$ is in the range | Extent of the increase: $\dot{m}_2(E)/\dot{m}_3(E)$ is in the range |
|---|---|
| from $>1.05 \cdot \dot{m}_2(A)$ to $1.50 \cdot \dot{m}_2(A)$ | from $1.03 \cdot \dot{m}_2(A)/\dot{m}_3(A)$ to $1.50 \cdot \dot{m}_2(A)/\dot{m}_3(A)$, especially $1.05 \cdot \dot{m}_2(A)/\dot{m}_3(A)$ to $1.50 \cdot \dot{m}_2(A)/\dot{m}_3(A)$ |

| Extent of the change in load: $\dot{m}_2(E)$ is in the range | Extent of the increase: $\dot{m}_2(E)/\dot{m}_3(E)$ is in the range |
|---|---|
| from >1.50 · $\dot{m}_2$ (A) to 2.00 · $\dot{m}_2$ (A) | from >1.50 · $\dot{m}_2$ (A)/$\dot{m}_3$ (A) to 2.00 · $\dot{m}_2$ (A)/$\dot{m}_3$ (A) |
| from > 2.00 · $\dot{m}_2$ (A) to 2.50 · $\dot{m}_2$ (A) | from >2.00 · $\dot{m}_2$ (A)/$\dot{m}_3$ (A) to 2.50 · $\dot{m}_2$ (A)/$\dot{m}_3$ (A) |

Here too, it is particularly preferable to keep $\dot{m}_3$ constant or at least essentially constant (i.e., more preferably, 0.98·$\dot{m}_3$ (A)≤$\dot{m}_3$ (E)≤1.02·$\dot{m}_3$ (A)). If $\dot{m}_3$ is kept the same, the percentage increase in load corresponds to the percentage increase in the ratio $\dot{m}_2/\dot{m}_3$. In the event of an increase in load to, for example, 125% of the starting value (i.e. $\dot{m}_2$ (E)=1.25·$\dot{m}_2$ (A)), the ratio $\dot{m}_2/\dot{m}_3$ is then likewise increased to 125% of the starting value (i.e. $\dot{m}_2$ (E)/$\dot{m}_3$ (E)=1.25·$\dot{m}_2$ (A)/$\dot{m}_3$ (A)).

Variant (c) of the invention is a combination of the aforementioned variants (a) and (b), i.e., in the event of a decrease in load, $\dot{m}_1$ (E)/$\dot{m}_2$ (E) is significantly increased and $\dot{m}_2$ (E)/$\dot{m}_3$ (E) is significantly decreased, in the event of an increase in load, $\dot{m}_1\dot{m}_1$ (E)/$\dot{m}_2$ (E) is significantly decreased and $\dot{m}_2$ (E)/$\dot{m}_3$ (E) is significantly increased.

Otherwise, the statements made above for variants (a) and (b) are correspondingly applicable.

In the event of a decrease in load, accordingly, it is preferably the case that:

| Extent of the change in load: $\dot{m}_2(E)$ is in the range | Extent of the increase: $\dot{m}_1$ (E)/$\dot{m}_2$ (E) is in the range | Extent of the decrease: $\dot{m}_2$ (E)/$\dot{m}_3$ (E) is in the range |
|---|---|---|
| from 0.80 · $\dot{m}_2$ (A) to <0.95 · $\dot{m}_2$ (A) to | from 1.03 · $\dot{m}_1$ (A)/$\dot{m}_2$ (A) to 1.20 · $\dot{m}_1$ (A)/$\dot{m}_2$ (A), especially 1.05 · $\dot{m}_1$ (A)/$\dot{m}_2$ (A) to 1.20 · $\dot{m}_1$ (A)/$\dot{m}_2$ (A) | from 0.80 · $\dot{m}_2$ (A)/$\dot{m}_3$ (A) to 0.97 · $\dot{m}_2$ (A)/$\dot{m}_3$ (A), especially 0.80 · $\dot{m}_2$ (A)/$\dot{m}_3$ (A) 0.95 · $\dot{m}_2$ (A)/$\dot{m}_3$ (A) |
| from 0.65 · $\dot{m}_2$ (A) to <0.80 · $\dot{m}_2$ (A) | from >1.20 · $\dot{m}_1$ (A)/$\dot{m}_2$ (A) to 1.40 · $\dot{m}_1$ (A)/$\dot{m}_2$ (A) | from 0.65 · $\dot{m}_2$ (A)/$\dot{m}_3$ (A) to <0.80 · $\dot{m}_2$ (A)/$\dot{m}_3$ (A) |
| from 0.40 · $\dot{m}_2$ (A) to <0.65 · $\dot{m}_2$ (A) | from >1.40 · $\dot{m}_1$ (A)/$\dot{m}_2$ (A) to 1.50 · $\dot{m}_1$ (A)/$\dot{m}_2$ (A) | from 0.40 · $\dot{m}_2$ (A)/$\dot{m}_3$ (A) to <0.65 · $\dot{m}_2$ (A)/$\dot{m}_3$ (A) |

In the event of an increase in load, it is preferably the case that:

| Extent of the change in load: $\dot{m}_2(E)$ is in the range | Extent of the decrease: $\dot{m}_1$ (E)/$\dot{m}_2$ (E) is in the range | Extent of the increase: $\dot{m}_2$ (E)/$\dot{m}_3$ (E) is in the range |
|---|---|---|
| from >1.05 · $\dot{m}_2$ (A) to 1.50 · $\dot{m}_2$ (A) | from 0.75 · $\dot{m}_1$ (A)/$\dot{m}_2$ (A) to 0.97 · $\dot{m}_1$ (A)/$\dot{m}_2$ (A), especially 0.75 · $\dot{m}_1$ (A)/$\dot{m}_2$ (A) to 0.95 · $\dot{m}_1$ (A)/$\dot{m}_2$ (A) | from 1.03 · $\dot{m}_2$ (A)/$\dot{m}_3$ (A) to 1.50 · $\dot{m}_2$ (A)/$\dot{m}_3$ (A), especially 1.05 · $\dot{m}_2$ (A)/$\dot{m}_3$ (A) to 1.50 · $\dot{m}_2$ (A)/$\dot{m}_3$ (A) |
| from >1.50 · $\dot{m}_2$ (A) to 2.00 · $\dot{m}_2$ (A) | from 0.55 · $\dot{m}_1$ (A)/$\dot{m}_2$ (A) to <0.75 · $\dot{m}_1$ (A)/$\dot{m}_2$ (A) | from >1.50 · $\dot{m}_2$ (A)/$\dot{m}_3$ (A) to 2.00 · $\dot{m}_2$ (A)/$\dot{m}_3$ (A) |
| from >2.00 · $\dot{m}_2$ (A) to 2.50 · $\dot{m}_2$ (A) | from 0.45 · $\dot{m}_1$ (A)/$\dot{m}_2$ (A) to <0.55 · $\dot{m}_1$ (A)/$\dot{m}_2$ (A) | from >2.00 · $\dot{m}_2$ (A)/$\dot{m}_3$ (A) to 2.50 · $\dot{m}_2$ (A)/$\dot{m}_3$ (A) |

Of the three variants (a), (b) and (c), variant (b) is the most preferable since the effect of the parameter $\dot{m}_2/\dot{m}_3$ is distinctly greater than the effect of the parameter $\dot{m}_1/\dot{m}_2$.

Irrespective of the variant chosen, the nitration of benzene to nitrobenzene is preferably conducted adiabatically and more preferably comprises the following steps:

(I) nitrating benzene with nitric acid and sulfuric acid to form nitrobenzene in a reactor, with introduction of a benzene-containing stream 10 with a mass flow rate of $\dot{m}_{10}$; a nitric acid-containing stream 20 with a mass flow rate of $\dot{m}_{20}$ and sulfuric acid-containing stream 30 with a mass flow rate of $\dot{m}_{30}$ into the reactor;

(II) separating the phases of the reaction mixture from step (I) in a phase separation apparatus into an aqueous, sulfuric acid-containing phase and an organic nitrobenzene-containing phase;

(III) concentrating the aqueous phase obtained in step (II) by evaporating water in an evaporation apparatus (the "flash evaporator") to give an aqueous sulfuric acid-containing phase having elevated sulfuric acid concentration, with recycling of the concentrated sulfuric acid-containing aqueous phase into step (I) and use thereof as a constituent of the sulfuric acid-containing stream 30;

(IV) washing, in at least two stages, the organic, nitrobenzene-containing phase obtained in step (II) and separating the aqueous phase off after each stage;

(V) distilling, preferably rectifying, the organic, nitrobenzene-containing phase obtained in the last stage of step (IV) with removal of unconverted benzene which is recycled into step (I) and used as a constituent of the benzene-containing stream 10, (VI) optionally and preferably working up the wastewater from the first wash stage of step (IV), comprising cleaning this wastewater in an apparatus for distillation or stripping, (VII) optionally and preferably working up the wastewater from the second wash stage of step (IV), comprising cleaning this wastewater in an apparatus for distillation or stripping, where an apparatus for thermal pressure decomposition may be connected up- and/or downstream of the apparatus for distillation or stripping.

Step (I) can in principle be conducted by any adiabatically operated nitration processes known from the prior art. For the execution of this step of the process of the invention, preference is given to using a tubular reactor in which multiple dispersing elements are arranged in distribution over the length of the reactor, which assure intensive dispersion and mixing of benzene, nitric acid and sulfuric acid. Such a reactor, and the form of usable dispersing elements, are described, for example, in EP 0708 076 B1 (FIG. 2) and EP 1 291 078 A2 (FIG. 1). Preferably, step (I) is executed in a process regime as described in DE 10 2008 048 713 A1, especially paragraph [0024].

The phase separation in step (II) is likewise effected by methods known per se from the prior art in a separation vessel known to those skilled in the art. The aqueous phase contains essentially sulfuric acid (diluted as a result of the formation of water of reaction) as well as inorganic impurities; the organic phase contains essentially nitrobenzene as well as excess benzene and organic impurities.

The concentration of the aqueous phase in step (III) is in principle effected as known from the prior art. The sulfuric acid in the aqueous phase is concentrated in a flash evaporator by evaporating water into a region of reduced pressure. Given correct choice of reaction conditions in the adiabatically implemented nitration of benzene with mixed acid, the heat of reaction of the exothermic reaction achieves such significant heating of the sulfuric acid-containing aqueous phase that, in the flash evaporator, the concentration and temperature of the sulfuric acid-containing aqueous phase that it had prior to the reaction with benzene and nitric acid on entry into the reactor space can simultaneously be established again. This is described, for example, in EP 2 354 117 A1, especially paragraph [0045]. The concentrated sulfuric acid thus obtained is recycled and used as a constituent of stream 30.

Preferably, step (IV) comprises the steps of (IVa) washing the organic nitrobenzene-containing phase obtained in step (II) in at least one wash, then separating the phases into an aqueous phase and an organic nitrobenzene-containing phase (first wash stage). The organic phase that typically still contains traces of acid is washed here, preferably in one to two washes, preferably one wash, with an aqueous washing liquid and is then separated from the acidic aqueous phase by phase separation (in the case of multiple washes after each individual wash). In this operation, the acid residues contained in the crude nitrobenzene are washed out; therefore, this process step is also referred to as acidic wash. The procedure here is preferably such that a pH<5 (measured at 20° C.) is established in the aqueous phase obtained after the phase separation in the acidic wash. The aqueous washing liquid used may be any kind of water, for example demineralized water or steam condensate. The water may also contain dissolved salts. Preferably, for performance of this acidic wash, aqueous streams obtained in operation are recycled.

(IVb) washing the organic phase obtained in step (IVa) in at least one alkaline wash with an aqueous solution of a base preferably selected from the group consisting of sodium hydroxide, sodium carbonate and sodium hydrogencarbonate, then separating the phases into an aqueous phase and an organic nitrobenzene-containing phase (second wash stage). Particular preference is given to using sodium hydroxide solution as aqueous base solution. The alkaline wash is described hereinafter for sodium hydroxide solution; it is a simple matter for the person skilled in the art to make appropriate alterations when other bases are used. The sodium hydroxide solution used preferably has a pH of 9.0 to 14 (measured at 20° C.). The mass ratio of sodium hydroxide solution to organic phase (essentially nitrobenzene) depends on the excess of benzene used in step (I) and is preferably 1:80 to 1:500. The pH of the sodium hydroxide solution used and its mass ratio to the organic phase are adjusted such that acidic impurities (for example nitrophenols formed as by-products and acid residues incompletely removed in step (II)) are largely to completely, preferably completely, neutralized in this alkaline wash. The subsequent workup of the alkaline wastewater can be effected by the methods of the prior art, for example according to EP 1 593 654 A1 and EP 1 132 347 A2. The organic, nitrobenzene-containing phase thus obtained preferably has a temperature of 20° C. to 60° C., more preferably of 30° C. to 50° C. It preferably contains, as well as nitrobenzene, 4.0% to 10% by mass of benzene, and less than 100 ppm, more preferably less than 60 ppm, of nitrophenols, based in each case on the total mass of the organic phase obtained.

(IVc) washing the organic phase obtained in step (IVb) in at least one neutral wash, preferably two to four neutral washes, more preferably two to three neutral washes, most preferably two neutral washes, with water, then separating the phases into an aqueous phase and an organic nitrobenzene-containing organic phase (third wash stage). This can in principle be accomplished by any methods that are customary in the prior art. The washing water used here is preferably demineralized water, more preferably a mixture of demineralized water and steam condensate (i.e. a condensate of steam which has been obtained by heat exchange of water with any exothermic process steps), and most preferably steam condensate. Preference is given to a procedure in which an electrophoresis is used in the last neutral wash (see WO 2012/013678 A2).

The washed nitrobenzene, in step (V), is finally freed of dissolved water, unconverted benzene and any organic impurities by further workup. This workup is effected by distillation, especially by rectification, wherein the vapors of water and benzene and any organic impurities are driven off overhead. The vapors are cooled and run into a separating vessel. Water separates out in the lower phase and is removed. In the upper phase are benzene and low boilers. This upper phase, optionally after further purification, is fed as return benzene back to the nitration in step (I), where it is part of stream 10. The distillation apparatus used is preferably a rectification column. The bottom product from the distillation, optionally after a further distillation in which nitrobenzene is obtained as distillate (i.e. as topstream or sidestream product), is sent to further applications (such as hydrogenation to aniline) as pure nitrobenzene.

The acidic aqueous phase from the wash from step (IVa), in a step (VI), is preferably freed of organics in an acidic wastewater workup and sent to a biological water treatment plant. The acidic wastewater workup especially comprises a wastewater reservoir tank, a heat exchanger, a wastewater distillation with condensation system, a wastewater condenser and an outlet to the acidic wash. The uncondensed vapors from the wastewater distillation, comprising benzene and nitrobenzene, are recycled into the wash in step (IV), especially into the acidic wash in step (IVa).

The alkaline aqueous phase from the wash from step (IVb), in a step (VII), is preferably freed of organics in an alkaline wastewater workup comprising a wastewater reservoir tank, a heat exchanger, a wastewater distillation with condensation system, and a system for thermal pressure decomposition. In the context of the present invention, thermal pressure decomposition is understood to mean a process for workup of alkaline wastewater in which organic impurities are decomposed under the action of elevated pressure and elevated temperature. Suitable processes are known to those skilled in the art and are described, for example, in EP 1 593 654 B1. In the context of the present invention, it is especially preferable to heat the alkaline wastewater (optionally pretreated in the apparatus for distillation or stripping), with exclusion of oxygen, to temperatures of 150° C. to 500° C. under an absolute pressure of 50 bar to 350 bar.

In spite of elevated amounts of aromatic and/or elevated amounts of sulfuric acid, it has been found that, surprisingly, the procedure of the invention brings a number of advantages that nevertheless make the process of the invention attractive:

i) The formation of by-products such as picric acid or nitrogen oxides ($NO_x$) is reduced.
ii) The sulfuric acid losses in the acidic wash are smaller.
iii) The large excess of benzene leads to better phase separation after the nitration and after the washes. This is especially true of the acidic wash (decrease in the risk of formation of a stable emulsion and hence impossibility of phase separation).
iv) The process of the invention offers a viable alternative to the shutdown of individual nitration lines operated in parallel in the event of a drop in demand. Rather than, for example, operating one of two nitration lines present at nameplate load and shutting down the other completely, it is possible by the process of the invention to operate both lines at half-load, which means that it is possible to avoid a costly, energy-intensive restart of the second nitration line when demand has risen again. This conserves all apparatus parts (for example pumps) that need not be shut down and put into operation again after a period of time.
v) As a result of the good product quality of the pure nitrobenzene even in part-load operation, advantages arise in respect of the use of such a nitrobenzene in further applications, especially in a catalytic gas phase aniline process. Additional impurities in the nitrobenzene heater and evaporator are avoided. In the case of injection of the nitrobenzene into a hydrogen gas stream, additional contamination of the catalyst surface that leads to a decrease in the selectivity and/or the lifetime of the catalyst is also avoided.

EXAMPLES

Content figures in ppm or % are parts by mass based on the total mass of the respective material/stream. Analysis values, unless stated otherwise, have been determined by means of high-performance liquid chromatography (HPLC—nitrophenols) and gas chromatography (GC—other by-products and benzene) and.

A. General Conditions for the Preparation of Nitrobenzene in Regular Operation at Nameplate Load Into a nitration reactor are metered a sulfuric acid stream ($\dot{m}_{30}$=210 t/h; $w_3$=0.713), a nitric acid stream ($\dot{m}_{20}$=10 000 kg/h; $w_2$=0.685) and a benzene stream ($\dot{m}_{10}$=9800 kg/h; $w_1$=0.989) consisting of 95% by mass of fresh benzene and 5% by mass of return benzene. A 14.14% excess of benzene is used, based on nitric acid. On completion of conversion of the nitric acid with the benzene to give nitrobenzene in an adiabatic reaction regime, the reaction product, now at about 130° C., is fed to a phase separation apparatus in which the reaction product separates into an organic phase (=crude nitrobenzene, also containing benzene as well as nitrobenzene) and an aqueous phase (=waste acid, also containing small proportions of nitrobenzene and benzene as well as sulfuric acid). The aqueous phase comprising mainly sulfuric acid is subjected to a flash evaporation of water by abruptly lowering the pressure in the evaporator, and concentrated in this way. The concentrated sulfuric acid is stored in the sulfuric acid tank for reuse. After being removed in the phase separation apparatus, the crude nitrobenzene is cooled down to about 50° C. in the crude nitrobenzene cooling operation and sent to the washing operation. This wash comprises an acidic wash stage, an alkaline wash stage and a neutral wash stage.

The stream of purified crude nitrobenzene which has been substantially freed of nitrophenols and salts and has been obtained in this way is heated up again and, in a distillation column, freed of water, benzene and other low boilers which are removed overhead, giving dried pure nitrobenzene. The condensed top product from the distillation column is fed to a phase separation apparatus in which the top product separates into an organic phase (comprising benzene) and an aqueous phase. The organic phase is stored intermediately in a buffer tank and thence run back, as already described above, into the feed of the nitration reactor for reaction.

The wastewater obtained in the alkaline wash is worked up as follows:

The wastewater from the alkaline wash is run into a settling tank in which undissolved benzene and nitrobenzene are separated out. 3.5 tonnes per hour of alkaline wastewater which has, on average, a nitrobenzene content of 2870 ppm, a benzene content of 409 ppm and a nitrophenols content of 11 809 ppm and a pH of 12.8 (1.8% excess of NaOH compared to the starting content of nitrophenols prior to the alkaline wash) are conducted into a stripping column in order to remove benzene and nitrobenzene from this alkaline wastewater overhead by stripping with steam. For this purpose, 500 kg/h of 6 bar steam are used. The pressure in the top of the column is 1.05 bar (absolute), and the temperature is 99.5° C. The top of the stripping column is equipped with a vertical condenser in which the benzene- and nitrobenzene-containing vapors are condensed out and then recycled into the acidic wash. The moist offgas at 99° C. from the stripping column is guided directly into the condenser and quenched by spraying with acidic water at 30° C. from the acid water tank. This prevents the possible deposition of ammonium nitrate and/or ammonium nitrite, which can form in the dry region of a conventional offgas conduit used for the separate conduction of the offgas out of the condenser (the ammonium salts mentioned may form from ammonia and nitrogen oxides present in the alkaline wastewater). The acidic water is fed to the acidic wash together with the condensed vapors. Any malfunction of the stripping column can be monitored, for example, by means of redundant safety devices. After the stripping, an alkaline wastewater that contains benzene only in a concentration of up to 10 ppm and nitrobenzene in a concentration of up to 10 ppm is obtained. Subsequently, the alkaline wastewater thus treated is treated in a plant for thermal pressure decomposition with a residence time of 20·min, a temperature of 290° C. and an absolute pressure of 90 bar. The wastewater that arises here is cooled down to 80° C. Thereafter, the wastewater is stripped with direct steam. In the bottoms from the stripping column, a stream of 4.0 tonnes per hour is obtained at an absolute pressure of 1.02 bar, which contains essentially water, ammonia, carbon dioxide and organics. The top product is condensed and cooled down to 35° C. A purge stream of organics is discharged from the condensate. 0.25 tonne per hour of the aqueous condensate stream depleted of organics is recycled into the stripping column as reflux. The proportion of organics in the wastewater obtained, which is sent to a biological water treatment plant, is 4726 ppm. The ammonium content in the wastewater is less than 87 ppm. In general, there are no problems at all with deposits in the region of the offgas from the stripping column.

Nitrobenzene prepared in this way has, on average, a purity of about 99.96% (GC), a residual benzene content of 0.0028% (GC) and a water content of 0.0079% (determined according to Karl Fischer). The following table summarizes the operating conditions at nameplate load:

TABLE 1

| Operating conditions at nameplate load | | | | | | | |
|---|---|---|---|---|---|---|---|
| $\dot{m}_{10}/$ (kg h$^{-1}$) | $w_1$ | $\dot{m}_{20}/$ (kg h$^{-1}$) | $w_2$ | $\dot{m}_1/\dot{m}_2$ | $\dot{m}_{30}/$ (t · h$^{-1}$) | $w_3$ | $\dot{m}_2/\dot{m}_3$ |
| 9800 | 0.989 | 10 000 | 0.685 | 1.41 | 210 | 0.713 | 0.0457 |

Notes:
$\dot{m}_1/\dot{m}_2 = \dot{m}_{10}/\dot{m}_{20} \cdot w_1/w_2$;
$\dot{m}_2/\dot{m}_3 = \dot{m}_{20}/\dot{m}_{30} \cdot w_2/w_3$.

B. Preparation of Nitrobenzene at Lower than Nameplate Load

All proportions by mass $w_i$ were kept the same with respect to operation at nameplate load.

Example 1 (Comparative): Decrease in Nitric Acid Load to about 93% of Nameplate Load with Corresponding Decrease in $\dot{m}_{10}$ and Corresponding Decrease in $\dot{m}_{30}$ Proceeding from production at nameplate load as described above under A, the mass flow rate $\dot{m}_{20}$ was reduced to 9301 kg/h (corresponding to $\dot{m}_{20}$ (E)/$\dot{m}_{20}$ (A)=$\dot{m}_2$ (E)/$\dot{m}_2$ (A)=0.9301). The mass flow rate $\dot{m}_{10}$ was reduced to 8954 kg/h, i.e. the ratio $\dot{m}_1$ (E)/$\dot{m}_2$ (E) was essentially maintained at 1.39 compared to the starting state.

The mass flow rate $\dot{m}_{30}$ was reduced to 195 t/h, i.e. the ratio $\dot{m}_2/\dot{m}_3$ was essentially maintained at 0.0458.

Example 2 (Inventive): Decrease in Nitric Acid Load to about 93% of Nameplate Load with Decrease in $\dot{m}_{10}$ and Retention of $\dot{m}_{30}$ Proceeding from production at nameplate load as described above under A, the mass flow rate $\dot{m}_{20}$ was reduced to 9298 kg/h (corresponding to $\dot{m}_{20}$ (E)/$\dot{m}_{20}$ (A)=$\dot{m}_2$ (E)/$\dot{m}_2$ (A)=0.9298). The mass flow rate $\dot{m}_{10}$ was reduced to 8937 kg/h, i.e. the ratio $\dot{m}_1$ (E)/$\dot{m}_2$ (E) was essentially maintained at 1.39 compared to the starting state. The slight nominal differences in $\dot{m}_{10}$ (E) and $\dot{m}_{20}$ (E) by comparison with example 1 do not impair comparability.

The mass flow rate $\dot{m}_{30}$ was kept constant, i.e. the ratio $\dot{m}_2/\dot{m}_3$ was decreased to 0.0425.

Example 3 (Comparative): Decrease in Nitric Acid Load to about 60% of Nameplate Load with Corresponding Decrease in $\dot{m}_{10}$ and Corresponding Decrease in $\dot{m}_{30}$ Proceeding from production at nameplate load as described above under A, the mass flow rate $\dot{m}_{20}$ was reduced to 6052 kg/h (corresponding to $\dot{m}_{20}$ (E)/$\dot{m}_{20}$ (A)=$\dot{m}_2$ (E)/$\dot{m}_2$ (A)=0.6052). The mass flow rate $\dot{m}_{10}$ was reduced to 5956 kg/h, i.e. the ratio $\dot{m}_1$ (E)/$\dot{m}_2$ (E) was essentially maintained at 1.42 compared to the starting state.

The mass flow rate $\dot{m}_{30}$ was reduced to 127 t/h, i.e. the ratio $\dot{m}_2/\dot{m}_3$ was kept essentially constant at 0.0458 compared to the starting state.

Example 4 (Inventive): Decrease in Nitric Acid Load to about 60% of Nameplate Load with Corresponding Decrease in $\dot{m}_{10}$ and (Essentially) Retention of $\dot{m}_{30}$ Proceeding from production at nameplate load as described above under A, the mass flow rate $\dot{m}_{20}$ was reduced to 6005 kg/h (corresponding to $\dot{m}_{20}$ (E)/$\dot{m}_{20}$ (A)=$\dot{m}_2$ (E)/$\dot{m}_2$ (A)=0.6005). The mass flow rate $\dot{m}_{10}$ was reduced to 5945 kg/h, i.e. the ratio $\dot{m}_1$ (E)/$\dot{m}_2$ (E) was essentially maintained at 1.43 compared to the starting state. The slight nominal differences in $\dot{m}_{10}$ (E) and $\dot{m}_{20}$ (E) by comparison with example 3 do not impair comparability.

The mass flow rate $\dot{m}_{30}$ was reduced only minimally to 207 t/h, i.e. the ratio $\dot{m}_2/\dot{m}_3$ was decreased to 0.0279 compared to the starting state.

Example 5 (Inventive): Decrease in Nitric Acid Load to about 60% of Nameplate Load with Increase in $\dot{m}_1/\dot{m}_2$ and (Essentially) Retention of $\dot{m}_{30}$ Proceeding from production at nameplate load as described above under A, the mass flow rate $\dot{m}_{20}$ was reduced to 6011 kg/h (corresponding to $\dot{m}_{20}$ (E)/$\dot{m}_{20}$ (A)=$\dot{m}_2$ (E)/$\dot{m}_2$ (A)=0.6011). The mass flow rate $\dot{m}_{10}$ was reduced to 6064 kg/h, i.e. the ratio $\dot{m}_1$ (E)/$\dot{m}_2$ (E) was increased to 1.46 compared to the starting state.

The mass flow rate $\dot{m}_{30}$ was reduced only minimally to 206 t/h, i.e. the ratio $\dot{m}_2/\dot{m}_3$ was decreased to 0.0280 compared to the starting state.

The following table compares the by-product contents to one another:

TABLE 2

| | By-product contents of nitrobenzene | | | | |
|---|---|---|---|---|---|
| Nitrobenzene from | $\dot{m}_1/\dot{m}_2$ compared to A | $\dot{m}_2/\dot{m}_3$ compared to A | $C_{1,3\text{-}DNB}/$ ppm | $C_{DNP}/$ ppm | $C_{PS}/$ ppm |
| Operation at nameplate load (A) | — | — | 250 | 1819 | 137 |
| Ex. 1 (comparative) | ess. the same | ess. the same | 316 | 2388 | 215 |
| Ex. 2 (inventive - variant (b)) | ess. the same | decreased | 284 | 1841 | 148 |
| Ex. 3 (comparative) | ess. the same | ess. the same | 522 | 2479 | 321 |

TABLE 2-continued

| | By-product contents of nitrobenzene | | | | |
|---|---|---|---|---|---|
| Nitrobenzene from | $\dot{m}_1/\dot{m}_2$ compared to A | $\dot{m}_2/\dot{m}_3$ compared to A | $C_{1,3\text{-}DNB}$/ ppm | $C_{DNP}$/ ppm | $C_{PS}$/ ppm |
| Ex. 4 (inventive - variant (b)) | ess. the same | decreased | 301 | 1945 | 162 |
| Ex. 5 (inventive - variant (c)) | increased | decreased | 289 | 1928 | 157 |

Notes:
ess. = essentially;
c = concentration;
DNB = dinitrobenzene;
DNP = dinitrophenol;
PS = picric acid.

It is immediately apparent that the reduction in load in all cases leads to increased by-product formation. However, the rise in the by-product content is considerably smaller in the case of the procedure of the invention than in the comparative experiments.

The invention claimed is:

1. A continuously operated process for preparing nitrobenzene, comprising nitrating benzene with nitric acid and sulfuric acid, wherein
   (i) the nitration is supplied with
      a stream containing benzene and having a proportion by mass of benzene $w_1$ with a mass flow rate of $\dot{m}_{10}$,
      a stream containing nitric acid and having a proportion by mass of nitric acid $w_2$ with a mass flow rate of $\dot{m}_{20}$, and
      a stream containing sulfuric acid and having a proportion by mass of sulfuric acid $w_3$ with a mass flow rate of $\dot{m}_{30}$;
   (ii) $\dot{m}_{10}$ and $\dot{m}_{20}$, for given values of $w_1$ and $w_2$, are chosen such that benzene is in a stoichiometric excess relative to nitric acid; and
   (iii) at least one change is made to the amount of nitric acid supplied to the nitration via $\dot{m}_{20}$
      from a starting state A defined by a mass flow rate of nitric acid $\dot{m}_2(A)=\dot{m}_{20}(A)\cdot w_2(A)$, a mass flow rate of benzene $\dot{m}_1(A)=\dot{m}_{10}(A)\cdot w_1(A)$ selected with regard to (ii) and a mass flow rate of sulfuric acid $\dot{m}_3(A)=\dot{m}_{30}(A)\cdot w_3(A)$,
      to a final state E defined by a desired mass flow rate of nitric acid $\dot{m}_2(E)=\dot{m}_{20}(E)\cdot w_2(E)$, a mass flow rate of benzene $\dot{m}_1(E)=\dot{m}_{10}(E)\cdot w_1(E)$ selected with regard to (ii) and a mass flow rate of sulfuric acid $\dot{m}_3(E)=\dot{m}_{30}(E)\cdot w_3(E)$,
   $\dot{m}_{20}$ and $w_2$ being chosen to establish the desired value for $\dot{m}_2(E)$
   wherein the at least one change in the amount of nitric acid supplied to the nitration via $\dot{m}_{20}$ is
   (1) a decrease to a value $\dot{m}_2(E)<0.95\cdot\dot{m}_2(A)$ for more than 0.50 hour
   or
   (2) an increase to a value $\dot{m}_2(E)>1.05\cdot\dot{m}_2(A)$ for more than 0.50 hour,
   wherein, in case (1)
   (a) the ratio $\dot{m}_1(E)/\dot{m}_2(E)$ is increased compared to $\dot{m}_1(A)/\dot{m}_2(A)$ such that:
      $1.03\cdot\dot{m}_1(A)/\dot{m}_2(A)\leq\dot{m}_1(E)/\dot{m}_2(E)\leq1.50\cdot\dot{m}_1(A)/\dot{m}_2(A)$
      and the ratio $\dot{m}_2(E)/\dot{m}_3(E)$ is altered to a maximum degree compared to the ratio $\dot{m}_2(A)/\dot{m}_3(A)$ such that:
      $0.98\cdot\dot{m}_2(A)/\dot{m}_3(A)\leq\dot{m}_2(E)/\dot{m}_3(E)\leq1.02\cdot\dot{m}_2(A)/\dot{m}_3(A)$
   or
   (b) the ratio $\dot{m}_2(E)/\dot{m}_3(E)$ is decreased compared to the ratio $\dot{m}_2(A)/\dot{m}_3(A)$ such that:
      $0.45\cdot\dot{m}_2(A)/\dot{m}_3(A)\leq\dot{m}_2(E)/\dot{m}_3(E)\leq0.97\cdot\dot{m}_2(A)/\dot{m}_3(A)$
      and the ratio $\dot{m}_1(E)/\dot{m}_2(E)$ is altered to a maximum degree compared to the ratio $\dot{m}_1(A)/\dot{m}_2(A)$ such that:
      $0.98\cdot\dot{m}_1(A)/\dot{m}_2(A)\leq\dot{m}_1(E)/\dot{m}_2(E)\leq1.02\cdot\dot{m}_1(A)/\dot{m}_2(A)$
   or
   (c) the ratio $\dot{m}_1(E)/\dot{m}_2(E)$ is increased compared to $\dot{m}_1(A)/\dot{m}_2(A)$ such that:
      $1.03\cdot\dot{m}_1(A)/\dot{m}_2(A)\leq\dot{m}_1(E)/\dot{m}_2(E)\leq1.50\cdot\dot{m}_1(A)/\dot{m}_2(A)$
      and the ratio $\dot{m}_2(E)/\dot{m}_3(E)$ is decreased compared to the ratio $\dot{m}_2(A)/\dot{m}_3(A)$ such that:
      $0.45\cdot\dot{m}_2(A)/\dot{m}_3(A)\leq\dot{m}_2(E)/\dot{m}_3(E)\leq0.97\cdot\dot{m}_2(A)/\dot{m}_3(A)$; and
   wherein, in case (2)
   (a) the ratio $\dot{m}_1(E)/\dot{m}_2(E)$ is decreased compared to $\dot{m}_1(A)/\dot{m}_2(A)$ such that:
      $0.45\cdot\dot{m}_1(A)/\dot{m}_2(A)\leq\dot{m}_1(E)/\dot{m}_2(E)\leq0.97\cdot\dot{m}_1(A)/\dot{m}_2(A)$
      and the ratio $\dot{m}_2(E)/\dot{m}_3(E)$ is altered to a maximum degree compared to the ratio $\dot{m}_2(A)/\dot{m}_3(A)$ such that:
      $0.98\cdot\dot{m}_2(A)/\dot{m}_3(A)\leq\dot{m}_1(E)/\dot{m}_3(E)\leq1.02\cdot\dot{m}_2(A)/\dot{m}_3(A)$
   or
   (b) the ratio $\dot{m}_2(E)/\dot{m}_3(E)$ is increased compared to the ratio $\dot{m}_2(A)/\dot{m}_3(A)$ such that:
      $1.03\cdot\dot{m}_2(A)/\dot{m}_3(A)\leq\dot{m}_2(E)/\dot{m}_3(E)\leq1.50\cdot\dot{m}_2(A)/\dot{m}_3(A)$
      and the ratio $\dot{m}_1(E)/\dot{m}_2(E)$ is altered to a maximum degree compared to the ratio $\dot{m}_1(A)/\dot{m}_2(A)$ such that:
      $0.98\cdot\dot{m}_1(A)/\dot{m}_2(A)\leq\dot{m}_1(E)/\dot{m}_2(E)\leq1.02\cdot\dot{m}_1(A)/\dot{m}_2(A)$
   or
   (c) the ratio $\dot{m}_1(E)/\dot{m}_2(E)$ is decreased compared to $\dot{m}_1(A)/\dot{m}_2(A)$ such that:
      $0.45\cdot\dot{m}_1(A)/\dot{m}_2(A)\leq\dot{m}_1(E)/\dot{m}_2(E)\leq0.97\cdot\dot{m}_1(A)/\dot{m}_2(A)$
      and the ratio $\dot{m}_2(E)/\dot{m}_3(E)$ is increased compared to the ratio $\dot{m}_2(A)/\dot{m}_3(A)$ such that:
      $1.03\cdot\dot{m}_2(A)/\dot{m}_3(A)\leq\dot{m}_2(E)/\dot{m}_3(E)\leq1.50\cdot\dot{m}_2(A)/\dot{m}_3(A)$.

2. The process of claim 1, wherein nitrating benzene to nitrobenzene is performed adiabatically.

3. The process of claim 2, wherein nitrating benzene to nitrobenzene comprises:
   (I) introducing a benzene-containing stream with a mass flow rate of $\dot{m}_{10}$, a nitric acid-containing stream with a mass flow rate of $\dot{m}_{20}$ and a sulfuric acid-containing stream with a mass flow rate of $\dot{m}_{30}$ into a reactor to form a reaction mixture;

(II) separating phases of the reaction mixture from step (I) in a phase separation apparatus into an aqueous sulfuric acid-containing phase and an organic nitrobenzene-containing phase;

(III) concentrating the aqueous phase obtained in step (II) by evaporating water in an evaporation apparatus to give an aqueous sulfuric acid-containing phase having elevated sulfuric acid concentration, and recycling the concentrated sulfuric acid-containing aqueous phase into step (I) as a constituent of the sulfuric acid-containing stream;

(IV) washing, in at least two stages, the organic nitrobenzene-containing phase obtained in step (II) and separating the aqueous phase off after each stage;

(V) distilling the organic nitrobenzene-containing phase obtained in the last stage of step (IV), and removing and recycling unconverted benzene into step (I) as a constituent of the benzene-containing stream.

4. The process of claim 3, further comprising:

(VI) working up wastewater from a first wash stage of step (IV) by cleaning the wastewater from the first wash stage in an apparatus for distillation or stripping, (VII) working up wastewater from a second wash stage of step (IV) by cleaning wastewater from the second wash stage in an apparatus for distillation or stripping, wherein an apparatus for thermal pressure decomposition is connected upstream and/or downstream from the apparatus for distillation or stripping.

5. The process of claim 3, further comprising:

(IVa) performing a first wash stage by washing the organic nitrobenzene-containing phase obtained in step (II) in at least one wash, then separating the phases into an aqueous phase and an organic nitrobenzene-containing phase;

(IVb) performing a second wash stage by washing the organic phase obtained in step (IVa) in at least one alkaline wash with an aqueous solution of a base, then separating the phases into an aqueous phase and an organic nitrobenzene-containing phase;

(IVc) performing a third wash stage by washing the organic phase obtained in step (IVb) in at least one neutral wash with water, then separating the phases into an aqueous phase and an organic nitrobenzene-containing organic phase.

6. The process of claim 1, wherein the ratio $\dot{m}_1$ (A)/$\dot{m}_2$ (A) is in the range from 1.26 to 1.74.

7. The process of claim 2, wherein:
$0.40 \cdot \dot{m}_2$ (A) $\leq \dot{m}_2$ (E) $\leq 2.50 \cdot \dot{m}_2$ (A).

8. The process of claim 7, wherein variant (a) is conducted, wherein, in case (1), the following relationships are applicable:

when $\dot{m}_2$ (E) is in the range from $0.80 \cdot \dot{m}_2$ (A) to $<0.95 \cdot \dot{m}_2$ (A), $\dot{m}_1$ (E)/$\dot{m}_2$ (E) is adjusted to a value in the range from $1.03 \cdot \dot{m}_1$ (A)/$\dot{m}_2$ (A) to $1.20 \cdot \dot{m}_1$ (A)/$\dot{m}_2$ (A);

when $\dot{m}_2$ (E) is in the range from $0.65 \cdot \dot{m}_2$ (A) to $<0.80 \cdot \dot{m}_2$ (A), $\dot{m}_1$ (E)/$\dot{m}_2$ (E) is adjusted to a value in the range from $>1.20 \cdot \dot{m}_1$ (A)/$\dot{m}_2$ (A) to $1.40 \cdot \dot{m}_1$ (A)/$\dot{m}_2$ (A);

and when $\dot{m}_2$ (E) is in the range from $0.40 \cdot \dot{m}_2$ (A) to $<0.65 \cdot \dot{m}_2$ (A), $\dot{m}_1$ (E)/$\dot{m}_2$ (E) is adjusted to a value in the range from $>1.40 \cdot \dot{m}_1$ (A)/$\dot{m}_2$ (A) to $1.50 \cdot \dot{m}_1$ (A)/$\dot{m}_2$ (A); or wherein, in case (2), the following relationships are applicable:

when $\dot{m}_2$ (E) is in the range from $>1.05 \cdot \dot{m}_2$ (A) to $1.50 \cdot \dot{m}_2$ (A), $\dot{m}_1$ (E)/$\dot{m}_2$ (E) is adjusted to a value in the range from $0.97 \cdot \dot{m}_1$ (A)/$\dot{m}_2$ (A) to $0.75 \cdot \dot{m}_1$ (A)/$\dot{m}_2$ (A);

when $\dot{m}_2$ (E) is in the range from $>1.50 \cdot \dot{m}_2$ (A) to $2.00 \cdot \dot{m}_2$ (A), $\dot{m}_1$ (E)/$\dot{m}_2$ (E) is adjusted to a value in the range from $0.55 \cdot \dot{m}_1$ (A)/$\dot{m}_2$ (A) to $<0.75 \cdot \dot{m}_1$ (A)/$\dot{m}_2$ (A);

and when $\dot{m}_2$ (E) is in the range from $>2.00 \cdot \dot{m}_2$ (A) to $2.50 \cdot \dot{m}_2$ (A), $\dot{m}_1$ (E)/$\dot{m}_2$ (E) is adjusted to a value in the range from $0.45 \cdot \dot{m}_1$ (A)/$\dot{m}_2$ (A) to $<0.55 \cdot \dot{m}_1$ (A)/$\dot{m}_2$ (A).

9. The process of claim 7, wherein variant (b) is conducted, wherein, in case (1), the following relationships are applicable:

when $\dot{m}_2$ (E) is in the range from $0.80 \cdot \dot{m}_2$ (A) to $<0.95 \cdot \dot{m}_2$ (A), $\dot{m}_2$ (E)/$\dot{m}_3$ (E) is adjusted to a value in the range from $0.80 \cdot \dot{m}_2$ (A)/$\dot{m}_3$ (A) to $0.97 \cdot \dot{m}_2$ (A)/$\dot{m}_3$ (A);

when $\dot{m}_2$ (E) is in the range from $0.65 \cdot \dot{m}_2$ (A) to $<0.80 \cdot \dot{m}_2$ (A), $\dot{m}_2$ (E)/$\dot{m}_3$ (E) is adjusted to a value in the range from $0.65 \cdot \dot{m}_2$ (A)/$\dot{m}_3$ (A) to $<0.80 \cdot \dot{m}_2$ (A)/$\dot{m}_3$ (A);

and when $\dot{m}_2$ (E) is in the range from $0.40 \cdot \dot{m}_2$ (A) to $<0.65 \cdot \dot{m}_2$ (A), $\dot{m}_2$ (E)/$\dot{m}_3$ (E) is adjusted to a value in the range from $0.40 \cdot \dot{m}_2$ (A)/$\dot{m}_3$ (A) to $<0.65 \cdot \dot{m}_2$ (A)/$\dot{m}_3$ (A); or wherein, in case (2), the following relationships are applicable:

when $\dot{m}_2$ (E) is in the range from $>1.05 \cdot \dot{m}_2$ (A) to $1.50 \cdot \dot{m}_2$ (A), $\dot{m}_2$ (E)/$\dot{m}_3$ (E) is adjusted to a value in the range from $1.03 \cdot \dot{m}_2$ (A)/$\dot{m}_3$ (A) to $1.50 \cdot \dot{m}_2$ (A)/$\dot{m}_3$ (A);

when $\dot{m}_2$ (E) is in the range from $>1.50 \cdot \dot{m}_2$ (A) to $2.00 \cdot \dot{m}_2$ (A), $\dot{m}_2$ (E)/$\dot{m}_3$ (E) is adjusted to a value in the range from $>1.50 \cdot \dot{m}_2$ (A)/$\dot{m}_3$ (A) to $2.00 \cdot \dot{m}_2$ (A)/$\dot{m}_3$ (A);

and when $\dot{m}_2$ (E) is in the range from $>2.00 \cdot \dot{m}_2$ (A) to $2.50 \cdot \dot{m}_2$ (A), $\dot{m}_2$ (E)/$\dot{m}_3$ (E) is adjusted to a value in the range from $>2.00 \cdot \dot{m}_2$ (A)/$\dot{m}_3$ (A) to $2.50 \cdot \dot{m}_2$ (A)/$\dot{m}_3$ (A).

10. The process of claim 7, wherein variant (c) is conducted, wherein, in case (1), the following relationships are applicable:

when $\dot{m}_2$ (E) is in the range from $0.80 \cdot \dot{m}_2$ (A) to $<0.95 \cdot \dot{m}_2$ (A), $\dot{m}_1$ (E)/$\dot{m}_2$ (E) is adjusted to a value in the range from $1.03 \cdot \dot{m}_1$ (A)/$\dot{m}_2$ (A) to $1.20 \cdot \dot{m}_1$ (A)/$\dot{m}_2$ (A) and $\dot{m}_2$ (E)/$\dot{m}_3$ (E) to a value in the range from $0.80 \cdot \dot{m}_2$ (A)/$\dot{m}_3$ (A) to $0.97 \cdot \dot{m}_2$ (A)/$\dot{m}_3$ (A);

when $\dot{m}_2$ (E) is in the range from $0.65 \cdot \dot{m}_2$ (A) to $<0.80 \cdot \dot{m}_2$ (A), $\dot{m}_1$ (E)/$\dot{m}_2$ (E) is adjusted to a value in the range from $>1.20 \cdot \dot{m}_1$ (A)/$\dot{m}_2$ (A) to $1.40 \cdot \dot{m}_1$ (A)/$\dot{m}_2$ (A) and $\dot{m}_2$ (E)/$\dot{m}_3$ (E) to a value in the range from $0.65 \cdot \dot{m}_2$ (A)/$\dot{m}_3$ (A) to $<0.80 \cdot \dot{m}_2$ (A)/$\dot{m}_3$ (A);

and when $\dot{m}_2$ (E) is in the range from $0.40 \cdot \dot{m}_2$ (A) to $<0.65 \cdot \dot{m}_2$ (A), $\dot{m}_1$ (E)/$\dot{m}_2$ (E) is adjusted to a value in the range from $>1.40 \cdot \dot{m}_1$ (A)/$\dot{m}_2$ (A) to $1.50 \cdot \dot{m}_1$ (A)/$\dot{m}_2$ (A) and $\dot{m}_2$ (E)/$\dot{m}_3$ (E) to a value in the range from $0.40 \cdot \dot{m}_2$ (A)/$\dot{m}_3$ (A) to $<0.65 \cdot \dot{m}_2$ (A)/$\dot{m}_3$ (A); or wherein, in case (2), the following relationships are applicable:

when $\dot{m}_2$ (E) is in the range from $>1.05 \cdot \dot{m}_2$ (A) to $1.50 \cdot \dot{m}_2$ (A), $\dot{m}_1$ (E)/$\dot{m}_2$ (E) is adjusted to a value in the range from $0.75 \cdot \dot{m}_1$ (A)/$\dot{m}_2$ (A) to $0.97 \cdot \dot{m}_1$ (A)/$\dot{m}_2$ (A) and $\dot{m}_2$ (E)/$\dot{m}_3$ (E) to a value in the range from $1.03 \cdot \dot{m}_2$ (A)/$\dot{m}_3$ (A) to $1.50 \cdot \dot{m}_2$ (A)/$\dot{m}_3$ (A);

when $\dot{m}_2$ (E) is in the range from $>1.50 \cdot \dot{m}_2$ (A) to $2.00 \cdot \dot{m}_2$ (A), $\dot{m}_1$ (E)/$\dot{m}_2$ (E) is adjusted to a value in the range from $0.55 \cdot \dot{m}_1$ (A)/$\dot{m}_2$ (A) to $<0.75 \cdot \dot{m}_1$ (A)/$\dot{m}_2$ (A) and $\dot{m}_2$ (E)/$\dot{m}_3$ (E) to a value in the range from $>1.50 \cdot \dot{m}_2$ (A)/$\dot{m}_3$ (A) to $2.00 \cdot \dot{m}_2$ (A)/$\dot{m}_3$ (A);

and when $\dot{m}_2$ (E) is in the range from >2.00·$\dot{m}_2$ (A) to 2.50·$\dot{m}_2$ (A), $\dot{m}_1$ (E)/$\dot{m}_2$ (E) is adjusted to a value in the range from 0.45·$\dot{m}_1$ (A)/$\dot{m}_2$ (A) to <0.55·$\dot{m}_1$ (A)/$\dot{m}_2$ (A) and $\dot{m}_2$ (E)/$\dot{m}_3$ (E) to a value in the range from >2.00·$\dot{m}_2$ (A)/$\dot{m}_3$ (A) to 2.50·$\dot{m}_2$ (A)/$\dot{m}_3$ (A).

11. The process of claim 9, wherein 0.98·$\dot{m}_3$ (A)≤$\dot{m}_3$ (E)≤1.02·$\dot{m}_3$ (A).

12. The process of claim 1, wherein $w_1$ (A)=$w_1$ (E) and/or $w_2$ (A)=$w_2$ (E) and/or $w_3$ (A)=$w_3$ (E).

13. The process of claim 12, wherein $w_1$ (A)=$w_1$ (E), $w_2$ (A)=$w_2$ (E) and $w_3$ (A)=$w_3$ (E).

14. The process of claim 1, comprising decreasing the amount of nitric acid supplied to the nitration via $\dot{m}_{20}$ in case (1), wherein decreasing is conducted by variant (b).

15. The process of claim 1, comprising increasing the amount of nitric acid supplied to the nitration via $\dot{m}_{20}$ in case (2), wherein increasing is conducted by variant (b).

* * * * *